(12) United States Patent
Stubblefield et al.

(10) Patent No.: US 12,037,466 B2
(45) Date of Patent: Jul. 16, 2024

(54) POLYMER RECYCLING

(71) Applicant: GEORGIA STATE UNIVERSITY RESEARCH FOUNDATION, INC., Atlanta, GA (US)

(72) Inventors: Bryan Stubblefield, Atlanta, GA (US); Eric Gilbert, Decatur, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 865 days.

(21) Appl. No.: 17/086,836

(22) Filed: Nov. 2, 2020

(65) Prior Publication Data
US 2021/0047494 A1 Feb. 18, 2021

Related U.S. Application Data

(62) Division of application No. 15/750,069, filed as application No. PCT/US2016/045586 on Aug. 4, 2016, now Pat. No. 10,822,469.

(60) Provisional application No. 62/200,916, filed on Aug. 4, 2015.

(51) Int. Cl.
| | |
|---|---|
| C12N 1/12 | (2006.01) |
| C08J 11/10 | (2006.01) |
| C08J 11/16 | (2006.01) |
| C08L 67/04 | (2006.01) |
| C12N 1/14 | (2006.01) |
| C12N 1/16 | (2006.01) |
| C12N 1/20 | (2006.01) |
| C12N 9/00 | (2006.01) |
| C12P 1/02 | (2006.01) |
| C12P 1/04 | (2006.01) |
| C12P 7/625 | (2022.01) |
| C12P 19/04 | (2006.01) |

(52) U.S. Cl.
CPC ............... *C08J 11/10* (2013.01); *C08J 11/16* (2013.01); *C08L 67/04* (2013.01); *C12N 1/12* (2013.01); *C12N 1/14* (2013.01); *C12N 1/16* (2013.01); *C12N 1/20* (2013.01); *C12N 9/00* (2013.01); *C12P 1/02* (2013.01); *C12P 1/04* (2013.01); *C12P 7/625* (2013.01); *C12P 19/04* (2013.01); *C08J 2377/02* (2013.01); *C08J 2377/06* (2013.01); *Y02W 30/62* (2015.05)

(58) Field of Classification Search
CPC ... C12N 1/14; C12N 1/16; C12N 1/20; C12N 9/00; C12P 7/625; C12P 19/04
See application file for complete search history.

(56) References Cited

U.S. PATENT DOCUMENTS

| | | | |
|---|---|---|---|
| 5,731,483 A | 3/1998 | Stabel et al. | |
| 7,129,190 B2 | 10/2006 | Takahashi | |
| 7,960,154 B1 | 6/2011 | Nakajima et al. | |
| 8,507,230 B2 | 8/2013 | O'Connor et al. | |
| 2004/0249001 A1 | 12/2004 | Leboeuf | |
| 2006/0106120 A1 | 5/2006 | Abe et al. | |
| 2015/0057379 A1 | 2/2015 | Bork et al. | |

FOREIGN PATENT DOCUMENTS

WO 2015067619 5/2015

OTHER PUBLICATIONS

International Search report and Written Opinion issued for International Application No. PCT/US2016/045586, dated Oct. 28, 2016, 9 pages.
International Preliminary Report on Patentability issued for International Application No. PCT/US2016/045586, dated Feb. 15, 2018, 7 pages.
Andreoni et al., International Biodeterioration & Biodegradation 31, 1993, 41-53.
Deguchi, et al., "Purification and Characterization of a Nylon-Degrading Enzyme", Applied Environ. Microbiol. Apr. 1998, 64(4), 1366-1371. p. 1366, col. 2 para.6.
Achilias, et al., "Chemical recycling of plastic wastes made from polyethylene (LDPE and HDPE) and polypropylene (PP)", J Hazard Mater 2007, 149:536-542.
Balasubramanian, et al., "Enhancement of in vitro high-density polyethylene (HDPE) degradation by physical, 290 chemical, and biological treatments". Environ Sci Pollut Res Int. 2014, 21:12549-12562.
Bogoczek, et la., "The use of supercritical fluids in the feedstock recycling of polymeric materials", Przem Chem 2006, 85:894-897.
Braunegg, et al., "A rapid gas chromatographic method for the determination of poly-ß-hydroxybutyric acid in microbial biomass." Eur J Appl Microbiol 1978, 6(1): 29-37.
Cregut, et al., "New insights into polyurethane 292 biodegradation and realistic prospects for the development of a sustainable waste recycling process", Biotechnol Adv 2013, 31:1634-1647.
Gaszczak, et al., "Kinetics of styrene biodegradation by 300 *Pseudomonas* sp. E-93486", Appl Microbiol Biotechnol 2012, 93:565-573.
Grause, et al., 2011. Feedstock recycling of waste polymeric material. J of Material Cycles and Waste Management 2011, 13:265-282.
Guzik, et al., "Conversion of post-consumer polyethylene to the biodegradable polymer 334 polyhydroxyalkanoate", Appl Biotechnol Microbiol 2014, 98:4223-4232.

(Continued)

*Primary Examiner* — Ruth A Davis
(74) *Attorney, Agent, or Firm* — Meunier Carlin & Curfman LLC

(57) ABSTRACT

Compositions and methods of making a culture medium from a polymeric material are described herein. The method can include (a) depolymerizing and/or dispersing the polymeric material to obtain a depolymerized and/or dispersed residue, and (b) combining the depolymerized and/or dispersed residue with one or more adjuvants to form a culture medium. In some embodiments, the polymeric material can be a plastic article, such as a waste carpet material. Culture media prepared from the compositions and methods are also described. The culture media are suitable for culturing microorganisms including bacterium, algae, and fungus. The microorganisms can be used to produce a bioproduct such as a biopolymer, an enzyme, or a cellular metabolite.

13 Claims, 13 Drawing Sheets

(56) References Cited

OTHER PUBLICATIONS

Hara, et al., "Transcriptomic analysis reveals 302 a bifurcated terephthalate degradation pathway in *Rhodococcus* sp. strain RHA1", J Bacteriol 2007, 189:1641-1647.

Keasling, JD. "Synthetic biology and the development of tools for metabolic engineering", Metab Eng 2012, 14:189-195.

Kenny, et al., "Up-cycling of PET (polyethylene terephthalate) to the biodegradable plastic PHA (polyhydroxyalkanoate)." Environ Sci Technol 2008, 42(20): 7696-7701.

Kim. "Properties and distribution of intracellular putrescine in a Pseudomonas", J Bacteriol 1965, 91:193-197.

Kyaw, et al., "Biodegradation of Low Density Polythene (LDPE) by *Pseudomonas* Species", Indian 296 J Microbiol 2012, 52:411-419.

Martinez-Garcia, et al., "New Transport tools tailored for metabolic engineering of gram-negative microbial cell factories", Frontiers in Bioeng. and Biotechnol. 2014, 2:46.

Martinez-Garcia, et al., "Pseudomonas 2.0: genetic upgrading of P. putida KT2440 as an enhanced host for heterologous gene expression", Microbial cell factories 2014, 13:159.

Mazzoli, et al., "Engineering new metabolic capabilities in bacteria: lessons from recombinant cellulolytic strategies", Trends in Biotechnol. 2012, 30: 111-119.

Negoro, S. "Biodegradation of nylon oligomers." Appl. Microbiol. Biotechnol 2000, 54(4): 461-466.

Negoro, "Biodegradation of nylon and other synthetic polyamides", Biopolymers Online. 9. 2005, Wiley-VCH Verlag GmbH & Co. KGaA.

Pittman, et al., "Agarose stabilization of fragile biofilms for quantitative structure analysis." Appl. Microbiol. Biotechnol 2010, 81(2): 101-107.

Rajoo, et al., "Isolation and characterization of a novel epsilon-caprolactam-degrading microbe, Acinetobacter calcoaceticus, from 306 industrial waste-water by chemostat-enrichment", Biotechnol Lett 2014, 35:2069-2072.

Sayyed, et al., "Hypochlorite digestion method for efficient recovery of PHB from Alcaligenes faecalis." Indian J Microbiol 2009, 49(3): 230-232.

Shukla, et al., "Depolymerization of nylon 6 waste fibers", J Appl Polym Sci. 2005, 100:186-190.

Sudhakar, et al., "Marine bacteria mediated degradation of nylon 66 and 6", Int Biodeterior Biodegrad 2007, 60:144-151.

Suzuki, et al., "Mass production of poly-ß-hydroxybutyric acid by fed-batch culture with controlled carbon/nitrogen feeding." Appl Biochem Biotech 1986, 24(5): 370-374.

Tokiwa, et al., "Biodegradability of plastics", Int J 298 Mol Sci 2009, 10:3722-3742.

Wang, et al., 2003, "Recycling of carpet and textile fibers", In Andrady AL (ed.), Plastics and The Environment: A Handbook. John Wiley and Sons. NY. pp. 697-725.

Wang. "Carpet recycling technologies. Recycling in textiles", Woodhead Publishing, Cambridge, England, 2006, 58-70.

Yasuhira, et al., "6-Aminohexanoate oligomer hydrolases from the alkalophilic bacteria *Agromyces* sp. strain KY5R and *Kocuria* sp. strain KY2", Appl Environ Microbiol 2007, 73:7099-7102.

POLYMER RECYCLING

CROSS REFERENCE TO RELATED APPLICATIONS

This application is a divisional of U.S. patent application Ser. No. 15/750,069 filed Feb. 2, 2018, which is a national stage application filed under 35 U.S.C. § 371 of PCT/US2016/045586 filed Aug. 4, 2016, which claims the benefit of U.S. Provisional Application No. 62/200,916 filed Aug. 4, 2015, which is hereby incorporated in its entirety and for all purposes.

FIELD OF THE DISCLOSURE

This disclosure relates generally to culture media, particularly to recycling polymeric materials for preparing culture media.

BACKGROUND OF THE DISCLOSURE

Polymeric materials such as plastics are highly useful, economical materials. In particular, plastics can be resistant to various types of environmental and chemical agents, thus allowing products made from them to maintain their integrity over long periods of time and over a wide variety of conditions. Additionally, many plastics are lightweight relative to their strength, making them practical for storage and transport. Conversely, the features that make plastics useful and economical result in their persistence and widespread distribution in the environment.

Commercially available plastics do not degrade or fully degrade in the environment. Typically, they are degraded through mechanical action into small pieces that retain their polymeric character. However, under natural conditions, microbial biotransformation of plastic polymers are generally limited. For example, as with many polymers, the large size of the molecules can interfere with uptake and catalysis by microorganisms. Additionally, the rate at which synthetic polymers are biodegraded may also be limited by their xenobiotic molecular structures. There is a need for reducing non-biodegradable materials in the environment. There is a particular need for methods for recycling polymeric materials. The compositions and methods described herein address these and other needs.

SUMMARY OF THE DISCLOSURE

Compositions and methods of making a culture medium from a polymeric material are described herein. The method can include (a) depolymerizing and/or dispersing the polymeric material to obtain a depolymerized and/or dispersed residue, and (b) combining the depolymerized and/or dispersed residue with one or more adjuvants to form a culture medium. The polymeric material can include a polyalkylene (e.g., polypropylene or polyethylene), polystyrene, polyurethane, polyester, nylon, polyimide, polyacrylate, polyalkylene terephthalate (e.g., polyethylene terephthalate), polyalkylene naphthalate (e.g., polyethylene naphthalate), polyolefin, polyacrylonitrile, rayon, polyether ketone, polyetherimide, polyamide-imide, polyvinylalcohol, polypeptide, protein, cellulose, wool, or a combination thereof. In some embodiments, the polymeric material can be a plastic article. In some examples, the plastic article can include a fibrous material. For example, the plastic article can be a carpet material including waste carpet fibers. Depolymerizing and/or dispersing the polymeric material can include contacting the polymeric material with a solvent to form a mixture. Depolymerizing and/or dispersing the polymeric material can further comprise heating the mixture of the polymeric material and the solvent. For example, the mixture can be heated to 50° C. or greater, such as from 50° C. to 300° C. (such as from 50° C. to 200° C.). The solvent can be an organic acid, an inorganic acid having a boiling point of 150° C. or less, a base, an oil, a non-polar organic solvent, or a combination thereof. Suitable examples of solvents used in depolymerizing and/or dispersing the polymeric material can include hydrochloric acid, acetic acid, formic acid, paraffin oil, olive oil, oleic acid, linoleic acid, palmitic acid, pristane, polyisobutene oil, hydrogenated polyisobutene oil, polydecene oil, polyisoprene oil, polyisopropene oil, fatty acids, vegetable oils, and combinations thereof. In some embodiments, the solvent can comprise a surfactant. The surfactant can be non-ionic, anionic, amphoteric, or cationic. In some embodiments, the surfactant is a biodegradable surfactant. In some examples, the solvent can include a non-ionic surfactant, an anionic surfactant, or a combination thereof.

The method of making the culture medium from a polymeric material can further include processing the depolymerized and/or dispersed residue prior to step (b). Processing the depolymerized and/or dispersed residue can include filtration, neutralization, evaporation, distillation, and/or rinsing the residue with a solvent.

One or more adjuvants may be added to the depolymerized and/or dispersed residue to obtain the culture medium. The one or more adjuvants can include water, acetate, lactose, glucose, fructose, maltose, ribose, a super optimal broth (SOB) media, a super optimal broth with catabolite repression (SOC) media, a nutrient broth, a nutrient agar, a minimal media, Luria-Bertani media, a sporulation broth, yeast extract, peptone, or combinations or modifications thereof. In some embodiments, the depolymerized and/or dispersed residue is combined with water or minimal media to obtain the culture medium.

In some embodiments, the method of making the culture medium from a polymeric material can include (a) heating the polymeric material with a solvent to depolymerize and/or disperse the polymeric material and form a mixture, (b) processing the mixture to form a resin, and (c) combining the resin with one or more adjuvants to form a culture medium. In some examples, the method can include melting the polymeric material prior to step (a) heating the polymeric material with a solvent.

Cultures prepared from the compositions and methods are also described herein. The culture medium can be prepared using any one of the methods described herein. In some embodiments, a culture medium for culturing a microorganism comprising one or more carbon sources, wherein the one or more carbon sources are derived from a polymeric material can be prepared using the methods described herein. In some embodiments, the one or more carbon sources include a monomer, an oligomer, or combinations thereof, derived from the polymeric material. For example, the one or more carbon source can include an amino acid, a dicarboxylic acid, an aminocarboxylic acid, a lactam, a diamine, a polyamine, or a combination thereof. In some embodiments, the carbon source can also serve as a nitrogen source for the culture medium.

The culture media described herein are suitable for culturing microorganisms including bacteria, algae, and fungi. In some embodiments, the microorganism can be a soil dwelling microorganism. For example, the microorganism can be a bacterium from the genus *Bacillus, Pseudomonas,*

*Streptomyces, Beijerinckia,* or *Rhodococcus.* Specific examples of bacteria include *Streptomyces coelicor, Bacillus subtilis, Bacillus licheniformis, Pseudomonas putida, Pseudomonas fluorescens, Beijerinkia indica,* and *Rhodococcus rhodochrous.* In some embodiments, the microorganism can be a fungus from the genus *Pichia, Rhodotorula, Candida, Aspergillus, Penicillium* or *Yarowia.* For example, the microorganism can be a lipid forming yeast. Specific examples of fungi include *Pichia pastoris, Rhodotorula glutinis, Candida maltosa, Aspergillus oryzae, Penicillium roqueforti,* and *Yarowia lipolytica.* In some embodiments, the microorganism can be an algae, such as from the genus *Chlorella.*

Also provided are methods for producing a biopolymer, an enzyme, or a cellular metabolite using the culture media described herein. The method for producing the biopolymer, enzyme or cellular metabolite can include introducing a host cell that expresses the desired product's biosynthetic pathway into the culture media, accumulating the product in the host cell by culturing the host cell, and recovering the product produced by the host cell. In some embodiments, the method for producing the biopolymer can include introducing a host cell that expresses the desired biopolymer's biosynthetic pathway into the culture media, accumulating the biopolymer in the host cell by culturing the host cell, and recovering the biopolymer produced by the host cell. The biopolymer can be any desirable polymer, including for example, a polyhydroxyalkanoate. In some embodiments, the method for producing the enzyme can include introducing a host cell that expresses the desired enzyme's biosynthetic pathway into the culture media, accumulating the enzyme in the host cell by culturing the host cell, and recovering the enzyme produced by the host cell. In some embodiments, the method for producing the cellular metabolite can include introducing a host cell that expresses the desired metabolite's biosynthetic pathway into the culture media, accumulating the cellular metabolite in the host cell by culturing the host cell, and recovering the cellular metabolite produced by the host cell. Any one of the microorganisms disclosed herein can be used as the host cell.

DETAILED DESCRIPTION

Figure 1:
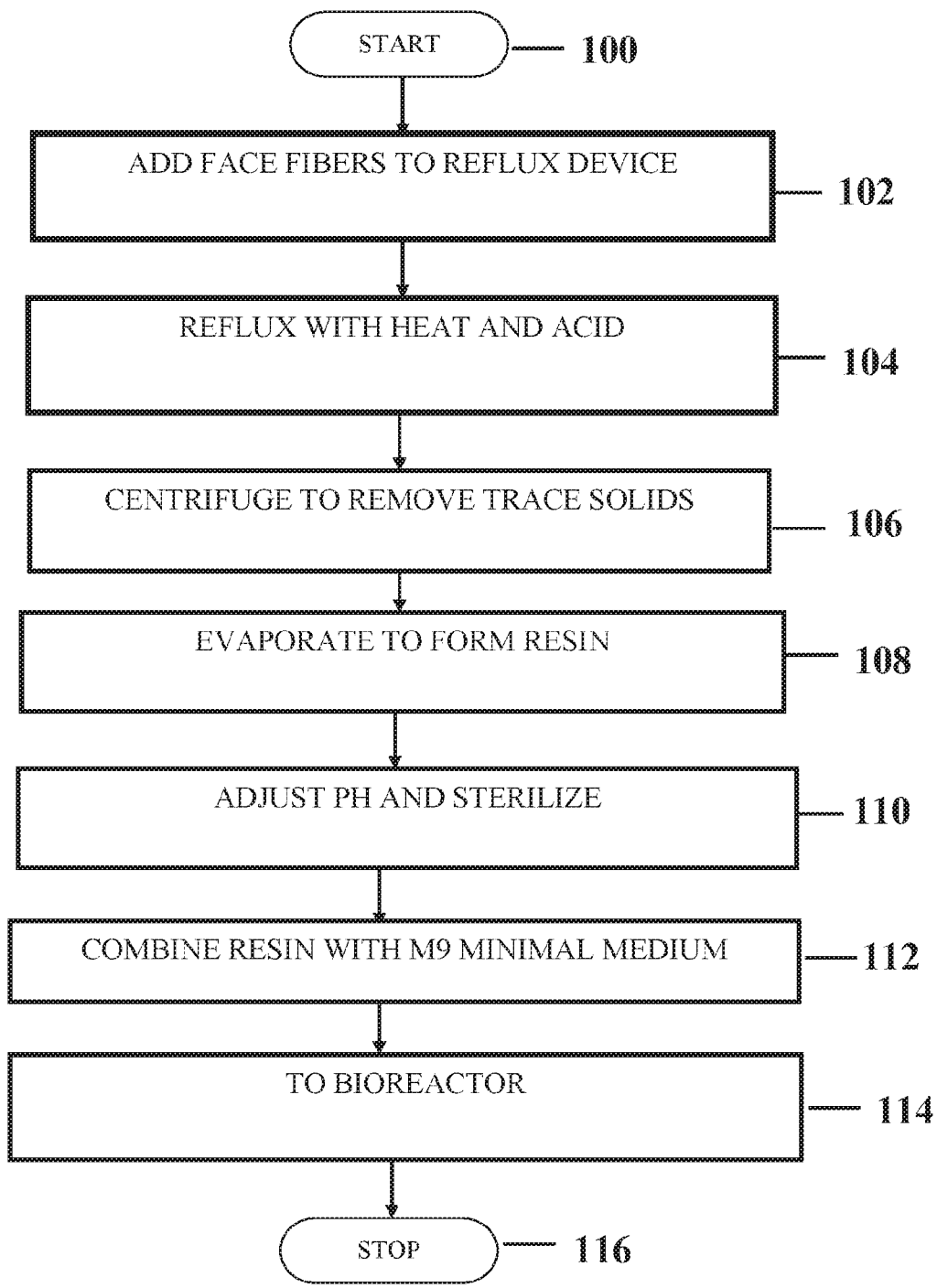
FIG. 1 is a flowchart depicting an exemplary method of preparing culture medium by acid hydrolysis.

Compositions and methods of processing a polymeric material are disclosed herein. The polymeric material can include natural or synthetic homopolymers or copolymers. The homopolymers or copolymers can be linear, branched, or cross-linked. In some embodiments, the polymeric material includes polyalkylene, polystyrene, polyurethane, polyester, nylon, polyimide, polyacrylate, polyalkylene terephthalate, polyalkylene naphthalate, polyolefin, polyacrylonitrile, rayon, polyetherimide, polyamide-imide, polyvinylalcohol, polypeptide, protein, cellulose, wool, or a combination thereof. In some examples, the polymeric material can include polyethylene, polypropylene, polybutylene, polyethylene terephtalate, polyethylene naphthalate, polylactic acid, nylon (polyamide) cellulose acetate, polycaprolactam, polylaurolactam, polyacrylamide, polystyrene, or a combination thereof. In some examples, the polymeric material includes nylon. The nylon can be derived from nylon 6, nylon 11, nylon 12, nylon 46, nylon 66, nylon 69, nylon 77, nylon 91, nylon 610, nylon 612, nylon 6/66, nylon 6/66/610, or combinations thereof.

In some embodiments, the polymeric material can include a homopolymer or copolymer derived from a monomer selected from an amino acid, a dicarboxylic acid, an aminocarboxylic acid, an amine, a diamine, and combinations thereof. For example, the homopolymer or copolymer can be derived from monomers selected from adipic acid, terephthalic acid, phthalic acid, isopthalic acid, aminoundecanoic acid, aminolauric acid, sebacic acid, dodecanoic acid, caprolactam, laurolactam, 6-aminohexanoic acid, hexamethylene amine, and combinations thereof.

In some embodiments, the polymeric material can be a plastic article, including thermoplastic articles. In some examples, the plastic article can include a fibrous material. For example, the plastic article can include natural or synthetic organic fibers of cellulose acetate, polyesters such as polyethylene terephthalate, synthetic polyamides such as polycaprolactam, polylaurolactam, or polyhexamethylene adipamide, or combinations thereof.

Suitable examples of plastic articles that can be processed using the methods described herein include plastic containers, packaging materials, credit cards, electronic components, construction materials, data storage devices, automotive and aircraft parts, floor coverings, adhesives, coatings, insulating foams, toys, appliances, telephones, machine screws, gear wheels, power tool casings, apparels and fabrics, carpet fibers, industrial waste plastic, and pipes. In some examples, the polymeric material can be a waste carpet material.

Solvents for processing the polymeric material are described herein. In some embodiments, the solvent can depolymerize and/or disperse the polymeric material. "Disperse" and "dispersing", as used herein, refer to the distribution of a particulate phase or phases, solid particles, or droplets, of the polymeric material throughout a liquid continuous phase. "Depolymerize" and "depolymerizing" as used herein, refer to degradation of a polymer into monomeric units, oligomeric units, polymeric units, and/or complete decomposition of the polymer. Depolymerization can occur by any suitable process known in the art, such as by hydrolysis, chain scission, or oxidation. Suitable solvents for processing the polymeric material can include an acid, a base, an oil, a non-polar organic solvent, and combinations thereof. In some examples, the solvent can include an acid having a boiling point of 150° C. or less. For example, the solvent can include inorganic acids such as hydrochloric acid, short chain organic acids such as formic acid, acetic acid, and combinations thereof. In some embodiments, the solvent can include a catalyst.

In some examples, the solvent can be an oil. "Oil", as used herein, can include fats, fatty substances, waxes, wax-like substances, and mixtures thereof. Suitable fats and fatty substances can include fatty alcohols (such as lauryl, myristyl, stearyl, cetyl or cetostearyl alcohol), fatty acids and derivatives, including but not limited to fatty acid esters, fatty acid glycerides (mono-, di- and tri-glycerides), and hydrogenated fats. Suitable waxes and wax-like materials include natural or synthetic waxes, hydrocarbons, and normal waxes. As used herein, a wax-like material is defined as any material which is normally solid at room temperature and has a melting point of from about 30 to 300° C. Specific examples of oils that can be used to process the polymeric material include paraffin oil, olive oil, polyisobutene oil, hydrogenated polyisobutene oil, polydecene oil, polyisoprene oil, polyisopropene oil, myristic acid, palmitic acid, oleic acid, linoleic acid, capric acid, lauric acid, neodecanoic acid, vegetable oils such as peanut oil, corn oil, and sesame oil, hydrogenated cottonseed oil, hydrogenated castor oil, hydrogenated oils available under the trade name Sterotex®, stearic acid, cocoa butter, stearyl alcohol, beeswax, glycowax, castor wax, carnauba wax, paraffins, candelilla wax, and mixtures thereof.

In some embodiments, the oil can include a surfactant. The surfactants can, in some embodiments, lower surface tension and thereby increase the emulsifying, foaming, dispersing, spreading, and wetting properties of the polymeric material in the oil. Suitable surfactants may be anionic, cationic, amphoteric, or nonionic surfactants. In some embodiments, the surfactant is biodegradable.

Suitable anionic surfactants include those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate, dialkyl sodium sulfosuccinates, and alkyl sulfates. Cationic surfactants include, but are not limited to, quaternary ammonium compounds such as polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates such as TWEEN® 20 (polysorbate 20) and TWEEN® 80 (polysorbate 20), polyoxyethylene octylphenylether, PEG-1000 cetyl ether, polyoxyethylene tridecyl ether, polypropylene glycol butyl ether, emulsifying wax, glyceryl monooleate, polyoxyethylene castor oil derivatives, benzyl alcohol, benzyl benzoate, cyclodextrins, stearoyl monoisopropanolamide, polyoxyethylene hydrogenated tallow amide, and combinations thereof. Examples of amphoteric surfactants include sodium N-dodecyl beta-alanine, sodium N-lauryl beta.-iminodipropionate, myristoamphoacetate, lauryl betaine and lauryl sulfobetaine. In some embodiments, the oil can include an anionic and non-ionic surfactant.

In some examples, the oil can include a surfactant selected from sodium lauryl sulfate (SLS), sodium dodecyl sulfate (SDS), sodium octyl sulfate (SOS), sodium bis-(2-ethylthioxyl)-sulfosuccinate, TWEEN® such as TWEEN® 20 (polysorbate 20) and TWEEN® 80 (polysorbate 80), fatty acids such as C8-C22 and other fatty acids, C8-C22 fatty alcohols, polyols, and combinations thereof.

In some embodiments, the oil can include a terpene. The terpene can, in some embodiments, increase the dispersing properties of the polymeric material in the oil.

Suitable terpenes can include monoterpenes. In some examples, the terpene can be derived from essential oils from plants. Culture media prepared from the polymeric material are described herein. The culture media can contain one or more carbon sources derived from the polymeric materials described herein. In some embodiments, the culture media can contain one or more carbon sources, wherein at least one of the one or more carbon sources can be derived from a carpet material such as a waste carpet material. In some embodiments, the one or more carbon sources can include a polymer, monomer, oligomer, or combinations thereof, which are derived from the polymeric material. For example, the one or more carbon sources can include an amino acid, a dicarboxylic acid, an aminocarboxylic acid, a lactam, an amine, a diamine, a polyamine, an alkene, an alkane, a polyalkylene, a ketone, an aldehyde, an oligomer or polymer thereof, or a combination thereof. Specific examples of the one or more carbon sources can include adipic acid, terephthalic acid, phthalic acid, isopthalic acid, aminoundecanoic acid, aminolauric acid, sebacic acid, dodecanoic acid, caprolactam, laurolactam, 6-aminohexanoic acid, hexamethylene amine, and combinations thereof.

The culture media can also contain a suitable adjuvant. The adjuvant can be selected from water, acetate, lactose, glucose, fructose, maltose, ribose, a super optimal broth (SOB) media, a super optimal broth with catabolite repression (SOC) media, a nutrient broth, a nutrient agar, a minimal media, Luria-Bertani media, a sporulation broth, yeast extract, peptone, and combinations or modifications thereof. In some embodiments, the culture media can include a carbon source derived from a polymeric material and an adjuvant selected from water, minimal salt media such as M9, and combinations thereof.

Methods of preparing culture media are described herein. The culture media can be prepared using any of the methods described herein. In some embodiments, methods of preparing a culture medium can include (a) depolymerizing and/or dispersing the polymeric material to obtain a depolymerized and/or dispersed residue, and (b) combining the depolymerized and/or dispersed residue with one or more adjuvants to form the culture medium. In certain embodiments, the residues obtained in step (a) include depolymerized residues. In certain embodiments, the residues obtained in step (a) include dispersed residues. In certain embodiments, the residues obtained in step (a) include depolymerized and dispersed residues. In some examples, the method can include the step of melting the polymeric material prior to step (a) depolymerizing and/or dispersing the polymeric material to obtain a depolymerized and/or dispersed residue. For example, a polymeric material containing nylon 66 can be heated to 260° C., the melting point of nylon 66, prior to depolymerizing and/or dispersing the nylon polymer.

Depolymerizing and/or dispersing the polymeric material can include contacting the polymeric material with a solvent to form a mixture. The solvent can include an organic acid, inorganic acid having a boiling point of 150° C. or less, a base, a non-polar organic solvent, an oil, or combinations thereof. In some embodiments, depolymerizing and/or dispersing the polymeric material can further include heating the mixture containing the polymeric material and the solvent. In some examples, the mixture can be heated up to the boiling point of the solvent. For example, the mixture can be heated to 50° C. or greater (for example, 75° C. or greater, 100° C. or greater, 150° C. or greater, 200° C. or greater, 300° C. or greater, 300° C. or less, 250° C. or less, 200° C. or less, 150° C. or less, 50° C. to 300° C., 50° C. to 250° C., or 50° C. to 200° C.).

The amount of solvent used during depolymerization and/or dispersion can be determined by one skilled in the art. In some embodiments, the solvent can be in an amount to facilitate optimal blending and/or dispersal of the polymeric material with the solvent. In some examples, the volume ratio of the solvent to the polymeric material can be from 10:1 or greater. For example, the volume ratio of the solvent to the polymeric material can be from 10:1 to 1000:1, such as 10:1 to 100:1 or 50:1 to 100:1. The mixture comprising the depolymerized and/or dispersed residues can be further processed prior to combining with the adjuvant. In some embodiments, the depolymerized and/or dispersed residues can be processed (for example, purified) prior to combining with the adjuvant. Processing the depolymerized and/or dispersed residue can include separating insoluble polymeric particles from the residues, neutralizing the mixture comprising the residues, washing the residues, removing the one or more solvents from the residues, and combinations thereof. In some examples, the depolymerized and/or dispersed residues can be processed by filtering, neutralizing, evaporating, distilling (including vacuum distillation), rinsing, and combinations thereof. The depolymerized and/or dispersed residues can be combined with one or more adjuvants described herein to form the culture medium. For example, the depolymerized and/or dispersed residues can be combined with water or minimal media.

In some examples, the method of making a culture medium from the polymeric material can include (a) heating the polymeric material with a solvent to depolymerize and/or disperse the polymeric material and form a mixture, (b) processing the mixture to form a resin, and (c) combining the resin with one or more adjuvants to form a culture medium. In some embodiments, the method can further include melting the polymeric material prior to step (a) heating the polymeric material with a solvent.

The methods described herein can be used for processing polymeric materials comprising polymers having low to high molecular weight. For example, the polymers can have molecular weights of 5,000 Da or greater, such as 10,000 Da or greater, 10,000 Da or greater, 50,000 Da or greater, 100,000 Da or greater, 250,000 Da or greater, or 500,000 Da or greater. In some embodiments, the polymers can have molecular weights of 500,000 Da or less, 250,000 Da or less, or 100,000 Da or less.

The polymeric material can be used to form culture media for culturing a microorganism. In some embodiments, the microorganism can include a bacterium, an algae, or a fungus. In some examples, the microorganism can be a soil dwelling microorganism. In some embodiments, the microorganism can be a bacterium of the genus *Bacillus, Pseudomonas, Streptomyces, Beijerinckia,* or *Rhodococcus*. For example, the bacterium can be selected from *Streptomyces coelicor, Bacillus subtilis, Bacillus licheniformis, Pseudomonas putida, Pseudomonas fluorescens, Beijerinckia indica, Rhodococcus rhodochrous,* and combinations thereof. In some embodiments, the microorganism can be a fungus of the genus *Pichia, Rhodotorula, Candida, Aspergillus, Penicillium* or Yarowia. For example, the fungus can be a lipid forming yeast. Specific examples of fungi include *Pichia pastoris, Rhodotorula glutinis, Candida maltosa, Aspergillus oryzae, Penicillium roqueforti,* and *Yarowia lipolytica*. In some embodiments, the microorganism can be an algae. Specific examples can include an algae from the genus *Chlorella*.

The polymeric material can also be used to produce a bioproduct, such as a biopolymer, an enzyme, or a cellular metabolite. In some embodiments, the polymeric material can also be used to produce a biopolymer. The biopolymer can be any desirable biopolymer including for example, a polyester (such as polyhydroxyalkanoate) or a polysaccharide. In some examples, the biopolymer can be polyhydroxybutyrate, polyhydroxyvalerate, a copolymer of poly(hydroxybutyrate-co-hydroxyvalerate), poly(3-hydroxybutyrate-co-4-hydroxybutyrate), or a copolymer of hydroxyl terminated polyhydroxybutyrate.

The method for producing the bioproduct can include introducing a host cell that expresses the bioproduct's biosynthetic pathway into a culture media as disclosed herein. The host cell can be any one of the microorganisms disclosed herein. For example, the host cell can be selected from a fungus, a bacterium, or an algae. In some embodiments, the host cell can contain one or more recombinant sequences that encodes the bioproduct's biosynthetic pathway.

The method for producing the bioproduct can include synthesizing and accumulating the bioproduct in the host cell by culturing the host cell. Suitable conditions for culturing the host cell can be readily identified by a person skilled in the art. For example, suitable conditions can include an appropriate medium that contains an appropriate carbon source as described herein and growing the host cell for a time sufficient to obtain expression of the required sequence (i.e., production of gene product) from the genes of the bioproduct's biosynthetic pathway, to produce the bioproduct. The bioproduct can then be recovered from the host cell. Recovering the bioproduct can include separating the bioproduct from the host cell, for example where the bioproduct is not extruded or secreted by action of the host cell during or after its production within the host cell.

In some embodiments, the method for producing the biopolymer can include introducing a host cell that expresses the desired biopolymer's biosynthetic pathway into the culture media, accumulating the biopolymer in the host cell by culturing the host cell, and recovering the biopolymer produced by the host cell. In some embodiments, the method for producing the enzyme can include introducing a host cell that expresses the desired enzyme's biosynthetic pathway into the culture media, accumulating the enzyme in the host cell by culturing the host cell, and recovering the enzyme produced by the host cell. In some embodiments, the method for producing the cellular metabolite can include introducing a host cell that expresses the desired metabolite's biosynthetic pathway into the culture media, accumulating the cellular metabolite in the host cell by culturing the host cell, and recovering the cellular metabolite produced by the host cell.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the disclosure. Unless indicated otherwise, parts are parts by weight, temperature is in ° C. or is at ambient temperature, and pressure is at or near atmospheric.

Example 1

Development of a Nylon-Based Growth Medium

Four different acid hydrolysis processes were developed, ranging from minimal to more extensive acid treatments, AH1 to AH4.

Chemicals: Caprolactam, adipic acid, hexametheylenediamine (HMDA), nylon 6,6 (N66), nylon 6 (N6), ninhydrin spray reagent 2%, HCl and $H_2SO_4$ were all purchased from Sigma-Aldrich, USA. M9 solution was prepared according to Handbook of Microbiological Media, third edition by Ronald M. Atlas. The M9 can be replaced with an autoclaved solution of 0.008 grams of yeast extract dissolved in 800 mL deionized water.

Preparation of AH1 medium: 10 mL of 5 M sulfuric acid ($H_2SO_4$) and 1 gram of N66 (nylon 66) pellets were added to a 100 mL Pyrex screwtop bottle. The mixture was allowed to stand for 24 hours then placed on a rotary shaker at 200 rpm for approximately 2 hours. The mixture was then added incrementally to 900 mL of distilled deionized water. The pH of the resulting mixture was adjusted to pH 6.8-7.5 by adding 10 M NaOH or NaOH pellets. M9 salts were added to the mixture to adjust the volume to 1000 mL and the pH adjusted again to pH 6.8-7.5 with 10 M NaOH or NaOH pellets. The mixture was autoclaved for 15 minutes at 15 psi and 121° C. then allowed to return to room temperature. The resulting mixture contained flocs ranging from 1-20 mm in diameter, with a whitish hue and various shapes.

Preparation of AH2 medium: 20 mL of glacial HCl or $H_2SO_4$, 20 mL of deionized water, and 1 gram of N66 pellets or carpet fibers were added to a Pyrex screwtop bottle. The mixture was placed on a rotary shaker at 250-300 rpm and allowed to shake for approximately 25 hours at room temperature. The mixture was then added to 900 mL of M9 solution after which the pH was adjusted to pH 7.5-8.0 by adding 10 M NaOH or NaOH pellets. The volume of the solution was adjusted to 1000 mL with M9 solution followed by autoclaving for 15 minutes at 15 psi and 121° C. then allowed to return to room temperature. The resulting mixture contained fine particles ranging from 2 mm in diameter or less, with a whitish hue.

Preparation of AH3 medium: 10 mL of glacial HCl, 10 mL of deionized water, and 1 gram of N66 pellets or carpet fibers were added to a Pyrex screwtop bottle. The mixture was allowed to stand for approximately 25 hours at room temperature. The mixture was transferred to a vacuum flask and connected to a vacuum line with trap in place. The vacuum flask was placed on a hotplate and the mixture stirred over mild heat (approximately 80° C.) until the solvent evaporated and the solution contained a fine resin. 100% Acetic acid (2 mL) was added to the resin while heating continued followed by addition of deionized water (150 mL). The mixture was filtered to remove chunks, if any were formed. The chunks were reprocessed as described above. 500 mL of M9 solution were added to the mixture after which the pH was adjusted to pH 6.8-7.5 by adding 1 M NaOH. The volume of the solution was adjusted to 1000 mL with M9 solution followed by autoclaving for 15 minutes at 15 psi and 121° C. then allowed to return to room temperature. The resulting mixture contained a few very fine flakes.

Preparation of AH4 medium: 100 mL of glacial HCl and deionized water (30:70 ratio) and 1 gram of N66 pellets or carpet fibers were added to a round bottom flask. The mixture was allowed to reflux for approximately 2-4 hours. The resulting mixture was filtered (0.22 micron filter) or centrifuged (13,000 rpm) to remove any residual particulates. The mixture was transferred to a beaker and the solvent boiled off for about 45 minutes to form a resin. Water or M9 (200 mL) was added to the resin and the pH adjusted to pH 6.8-7.5 using 1 M NaOH solution. The mixture was filtered using a 0.22 micron filter. 800 mL of autoclaved M9 solution was added to the mixture after which the pH was adjusted to pH 6.8-7.5 by adding 1 M NaOH. The volume of the solution was adjusted to 1000 mL with an autoclaved modified M9 solution (containing no magnesium salts and supplemented with 1 mg per liter of yeast extract) that was added to the mixture. The preparation of the AH4 medium is detailed in FIG. 1.

Characterization of the Nylon-Based Media Composition

Electrospray injection mass spectrometry: Electrospray injection mass spectrometry (ES1-MS) was conducted using a Waters Q-TOF micro mass spectrometer equipped with an electrospray ionization source (ESI) in negative ion or positive mode (Waters, Milford, MA). The instrument was calibrated with sodium formate and the mass range was from 100-1000 Da. The sample was introduced into the ion source through direct infusion at a flow rate of 5 µL min$^{-1}$. Data were analyzed using Masslynx 4.1 software.

LPLC Fractionation for Analysis of AH4 Composition and Biodegradation

Low pressure liquid chromatography: Low pressure liquid chromatography (LPLC) was used to separate the AH4 medium in order to characterize its chemical composition. Two stationary phases were used: a methyl-based hydrophobic resin (Macro-prep Methyl HIC support, 156-0080; Bio-Rad, USA) was used to examine the chemical composition of AH4; and Davisil silica gel, 60-70 mesh (Grace, USA) was used to measure substrate biodegradation during P. putida KT2440 growth. Columns were made from 3 mL polypropylene plastic syringes with the plunger removed and with the needle opening plugged with glass wool. Each column was dry packed with 100% 2-propanol at a flow rate of 1 mL min$^{-1}$. After packing the column to the 1 mL mark, a 2-3 mm layer of sand was layered on top to keep the column level. Columns were allowed to equilibrate with the mobile phase. For columns packed with the hydrophobic resin, the mobile phase was 50% ethanol. For columns packed with silica gel, the mobile phase consisted of 3:1:1 2-propanol: acetic acid: ultrapure distilled deionized water (DDH$_2$O). Each time prior to use, columns were washed with 40 volumes of mobile phase. A Masterflex model 77521-50 peristaltic pump was used to add the sample to the column with a flow rate of 1 mL min$^{-1}$ (Cole-Parmer, USA). A constant flow rate was maintained over the course of experiments. A total of 1 mL of sample was loaded on the column and for each experiment, 1 mL fractions were obtained.

With the exception of adipic acid, the collected fractions were complexed with ninhydrin for analysis by spectrophotometer. 100 μl of sample was mixed with 25 μl of a 0.01% ninhydrin solution and 50 μl of DDH2O in a 1.5 mL microfuge tube. Tubes were mixed for 15 minutes at 300 rpm at 98-99° C. The samples were transferred to 96-well microtiter plates and scanned at 570 nm on a SpectraMax 190 plate reader (Molecular Devices, USA). Adipic acid samples were complexed with 20 mg L$^{-1}$ bromothymol blue and were imaged at 430 nm (presence of carboxyl groups) and 620 nm (absence of carboxyl groups) by spectrophotometer.

Bacterial Growth and Substrate Metabolism in Nylon-Based Growth Media:

Inocula preparation: All bacteria were stored at -80° C. Pseudomonas putida KT2440 was cultivated from stock originating in the ATCC culture collection. Inocula were grown overnight from frozen stock in 30-50 mL LB broth in an Erlenmeyer flask at 30° C. The resulting cell suspension was washed once in M9 or 50 mM phosphate buffer prior to use.

Bioreactor operation: A 450 mL bioreactor was used for growth experiments. All components of the bioreactor were autoclaved prior to use. Growth experiments were conducted at 30° C. with a mixing speed of 150 rpm. The pH of the medium was maintained at 7.2 to 7.5. Filter sterilized sparged air was continuously added to the bioreactor. The average duration of each reaction was 7-11 days. The bioreactor was sampled via a sampling port and data on pH and temperature were continuously collected via a data logging device.

LPLC-ninhydrin assay: Low pressure liquid chromatography (LPLC) was used to separate interfering chemicals away from AH4 depolymerized resin prior to measuring the extent of substrate biodegradation by Pseudomonas putida KT2440 in the bioreactor. A methyl-based hydrophobic resin was used for the separation (Bio-Rad, USA), and the technique is referred to as hydrophobic interaction chromatography (HIC) throughout this example. Collected fractions were stained with ninhydrin, a dye which binds to amine groups, which are believed to be a common component of the AH4 depolymerized resin. The absorbance of the ninhydrin-stained AH4 depolymerized resin was measured by spectrophotometer at 570 nm and concentrations were resolved by use of a standard curve.

Column preparation and operation: The LPLC column was made from a 3 mL polypropylene plastic syringe with the plunger removed. The needle opening was plugged with glass wool to keep the stationary phase inside. The stationary phase was composed of 1 gram of Davidson silica gel 60-70 mesh. The column was dry packed with 100% 2-propanol at a flow rate of 1 mL min$^{-1}$. After packing the column to the 1 mL mark, a 2-3 mm layer of pure sand was layered on top to keep the column level. The column was allowed to equilibrate with the mobile phase, which consisted of 3:1:1 2-propanol: acetic acid: ultrapure distilled deionized water. Each time prior to use, the column was washed with 40 volumes of mobile phase. The pump set up was as follows: a Coleman peristaltic pump was used with a flow rate of 1 mL min$^{-1}$.

A total of 1 mL of sample was loaded on the silica gel column with the liquid phase level brought down to 1 mL from the top of the sand of the solid phase. The mobile phase was allowed to double in volume to 2 mL in the 3 mL column before starting the fractionation of the sample. From each experiment, 1mL fractions were obtained. Collected fractions were complexed with ninhydrin for analysis by spectrophotometer. The ninhydrin reaction was carried out as follows: 100 μL of sample was mixed with 25 μL of a 0.01% ninhydrin solution and 50 μL of deionized water in a 1.5 mL microfuge tube. Tubes were mixed for 15 minutes at 300 rpm at 98-99° C. The samples were transferred to 96 well microtiter plates and scanned at 570 nm on a Victor$^3$ plate reader.

Viscometry: Polymer concentrations in solution can be measured by viscometry, with higher concentrations typically having greater viscosity. Changes in the viscosity of AH4 medium during growth were measured with a Cannon-Fenske tube size 200 viscometer (Sigma-Aldrich, USA). The viscometer was calibrated using DDH$_2$O and a minimum of 3 replicate measurements were made per timepoint. Samples from the bioreactor and from flasks were centrifuged at 20,400×g for 5 minutes to remove cells prior to analysis. The relative viscosity, lir, was determined by normalizing each day's measurements to the viscosity of DDH$_2$O.

Substrate mass measurements: The mass of carpet fibers used to prepare each batch of AH4 medium was determined prior to processing. The mass of the resin produced from each batch of carpet fiber was also weighed. The mass of solids in the resin was determined by thermal decomposition of the resin using a Corning PC 420 hot plate (Corning, USA) set to maximum for 4 min and weighing the remaining residue.

Figure 3:
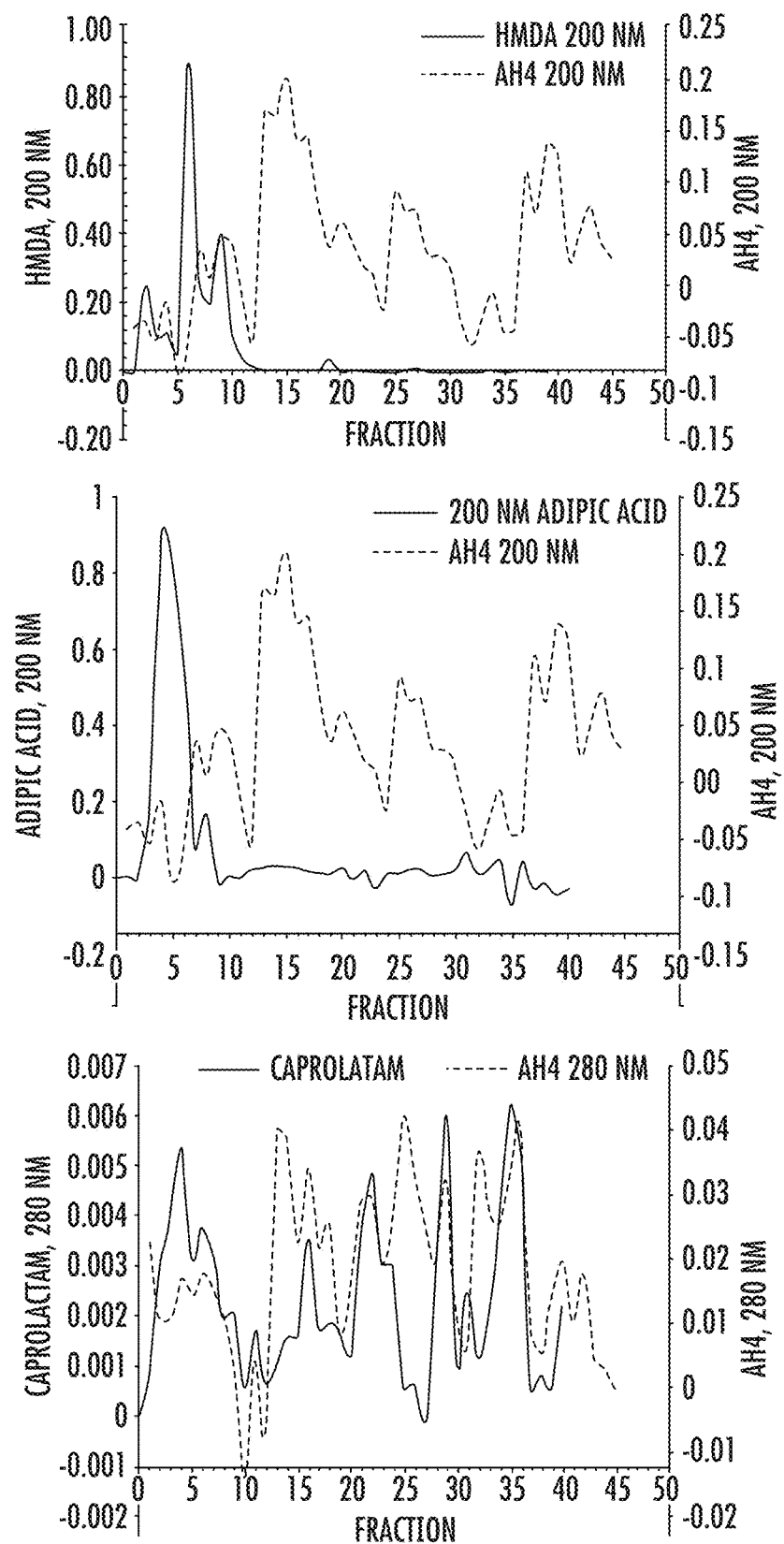
FIG. 3 are graphs showing a comparison of AH4 medium with authentic standards (top: hexamethylene diamine; middle: adipic acid; bottom: caprolactam). Analysis was conducted using LPLC spectrophotometry.

Results:

The composition of AH4 medium was analyzed with two approaches, LPLC-spectrophotometry and ESI-MS. First, LPLC was used to fractionate AH4 medium. The absorbance of each fraction was measured spectrophotometrically at 200 nm and 280 nm (FIG. 3). Three standards (adipic acid, HMDA, and caprolactam) prepared from authentic chemicals were fractionated and measured in an identical manner such that their spectra could be compared to the AH4 medium. Peaks in the AH4 medium with similar absorption characteristics to the standards were evident, indicating the presence of adipic acid, HMDA, caprolactam, and/or structurally similar compounds in the medium.

Figure 4:
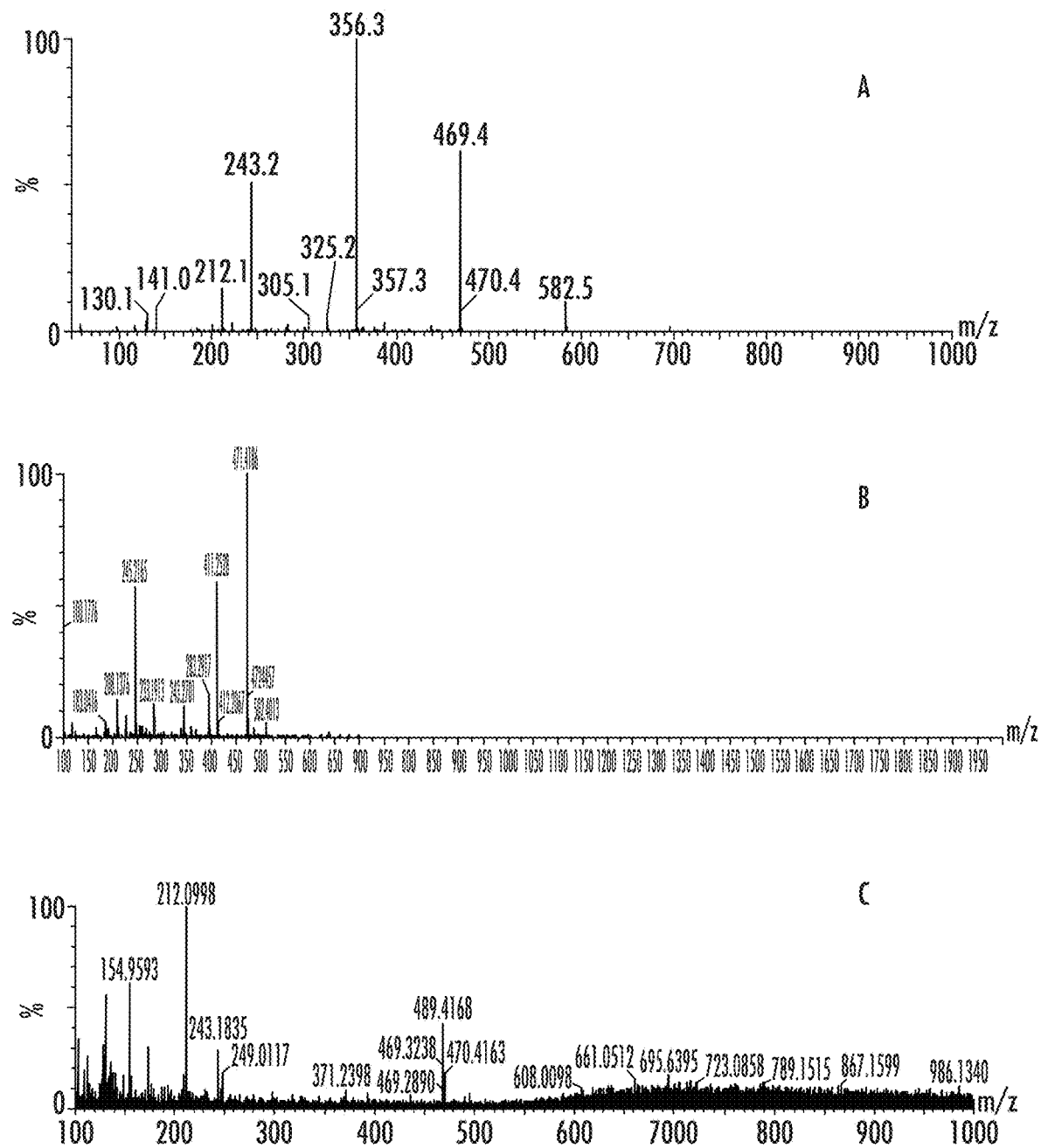
FIG. 4 are graphs showing ESI-MS analysis of the composition of AH4 (panels A and B) and acid-hydrolyzed nylon-wool carpet fiber (panel C)..

Next, the composition of the AH4 medium was analyzed by ESI-MS (FIG. 4A). The N66 monomer, comprised of adipic acid-HMDA (M=262), was evident with an m/z ratio of 243 (M-H$_2$O—H). Ion fragments separated by m/z values of 113 were evident at 356, 469, and 582, indicating molecules with varying numbers of HMDA fragments. The maximum m/z ratio of components in the mixture was 582. The data indicated that the medium was comprised of a heterogeneous mix of molecules comprised primarily of N66 monomer, HMDA-adipic acid-HMDA, and N66 dimer, or structurally related molecules.

The mass of acid-hydrolyzed carpet face fiber contained in AH4 medium was determined. First, the mass of carpet fiber used to prepare a batch of AH4 medium with a concentration of 1 g L$^{-1}$ was compared to the mass of the corresponding derived resin following acid hydrolysis. In three replicate experiments, the mass of the resin was 122±7 percent of the initial carpet fiber mass. Subsequently, the resin was heated to remove water.

After heating, the remaining mass was 106±17 percent of the initial carpet fiber mass. ESI-MS was used to determine the size range of molecules in AH4 medium. Scans from 0-1950 m/z indicated that the largest components of AH4 medium had an m/z ratio of 800 (FIG. 4B). Visual inspection indicated that the resin dissolved completely in the M9 solution used for preparing AH4 medium.

Figure 5:
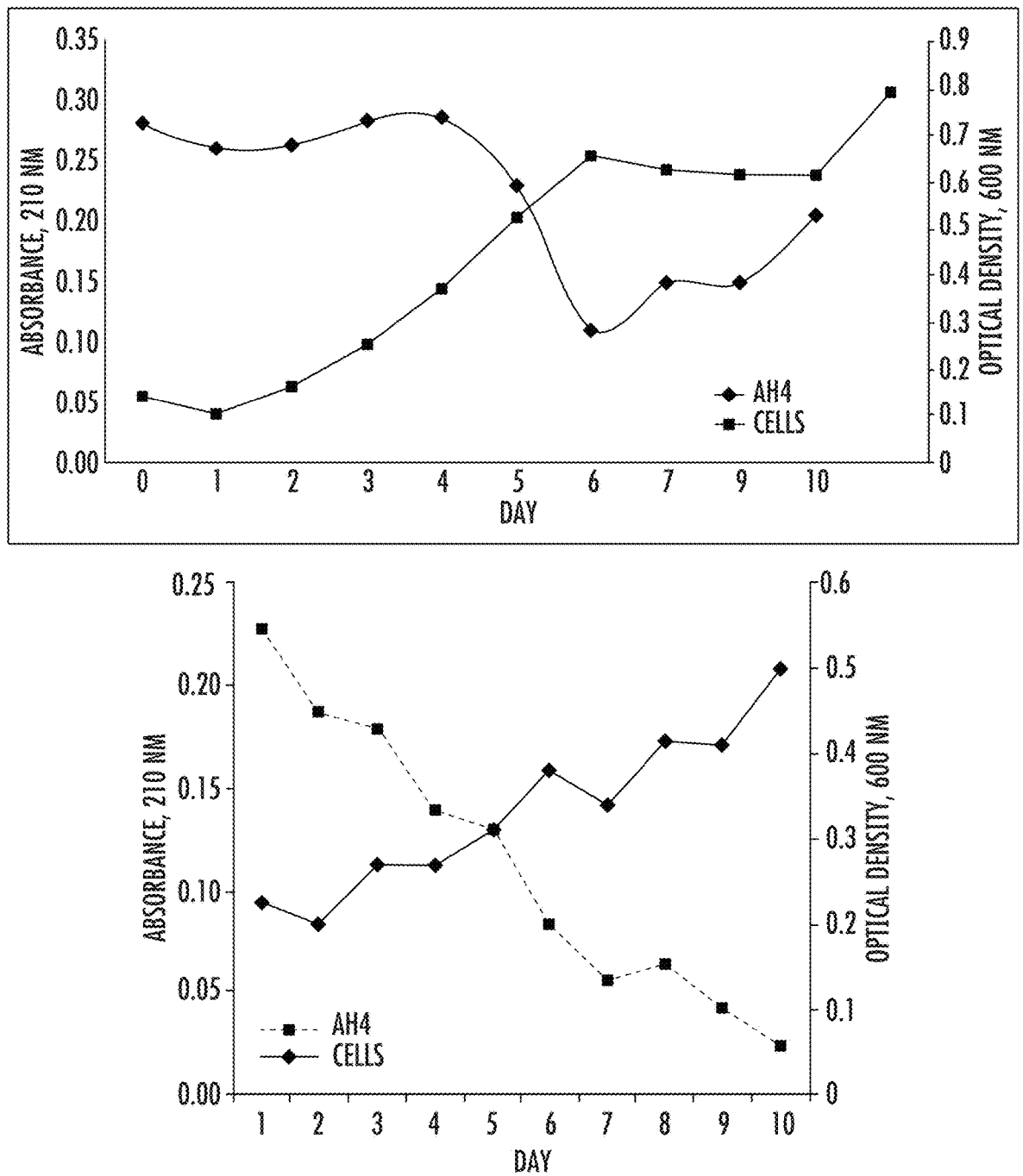
FIG. 5 are graphs showing *P. putida* KT2440 growth in a bioreactor using AH4 medium. Black line, growth (optical density, 600 nm). Gray line, substrate utilization (AH4 concentration, 210 nm). The experiments represented by the top and bottom graphs were conducted five months apart.
Figure 6:
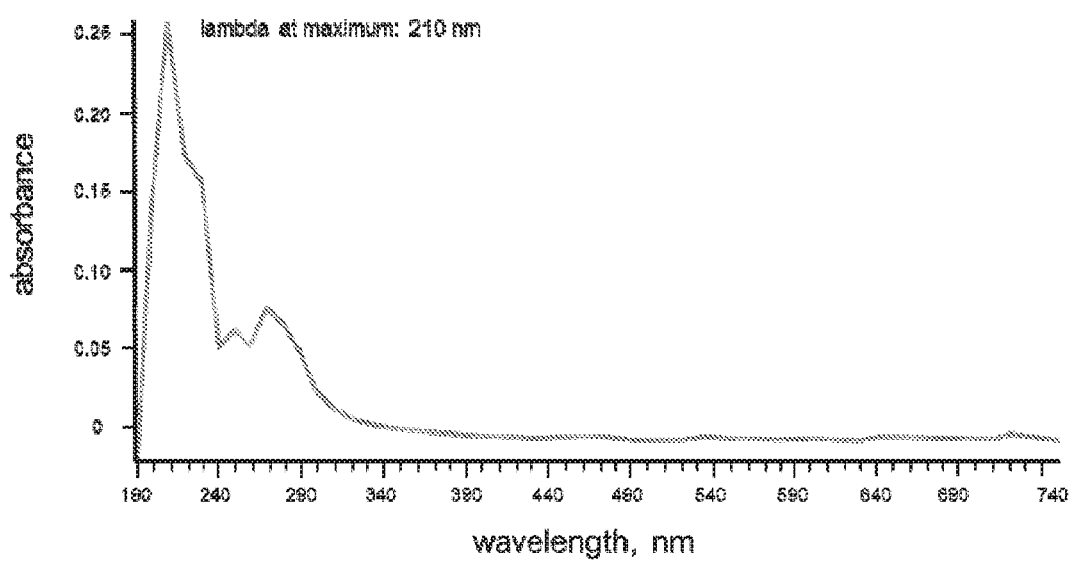
FIG. 6 is a graph showing an absorbance spectrum of AH4 substrate medium. Maximum absorbance was detected at 210 nm.
Figure 7:
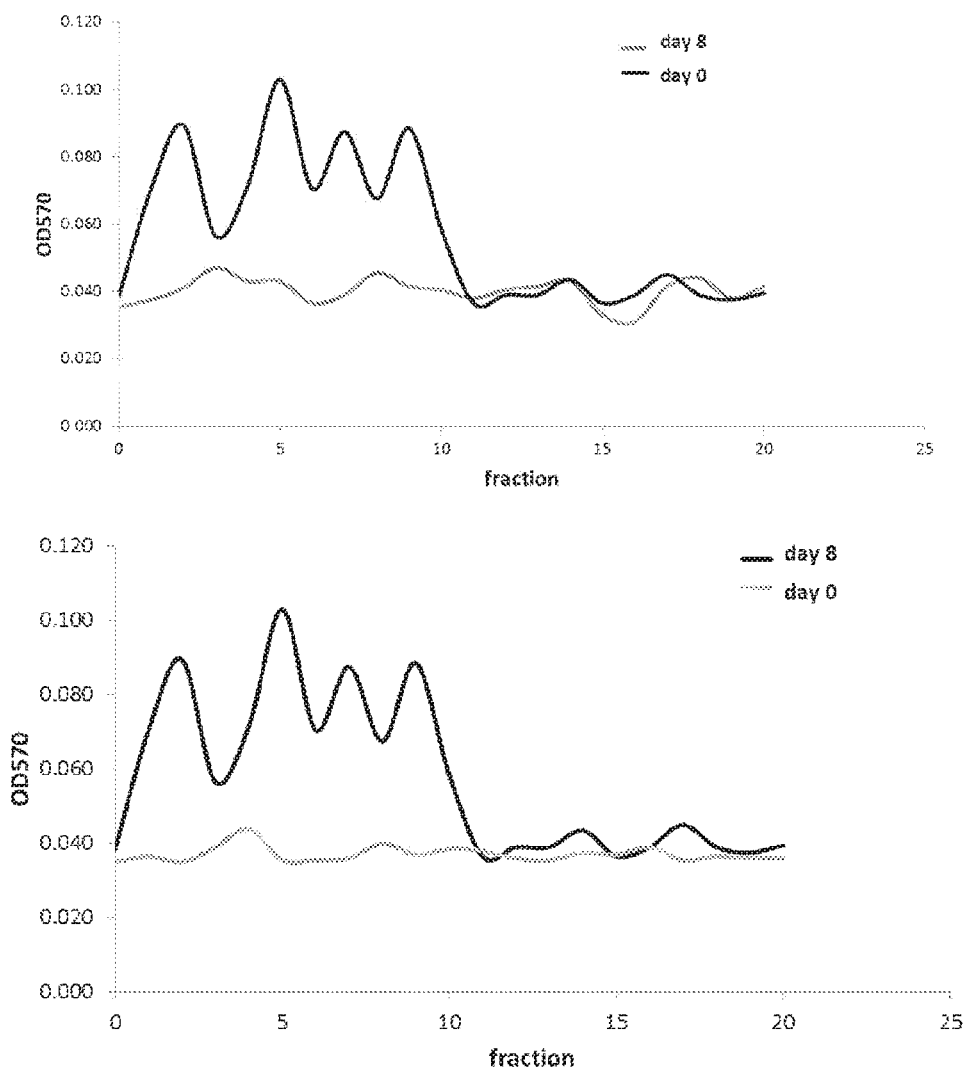
FIG. 7 are graphs showing LPLC spectrophotometric analysis of AH4 substrate utilization by *P. putida* KT2440 during bioreactor growth. Both independent bioreactor experiments were conducted at separate times.

To determine the extent to which AH4 could serve as a growth substrate for P. putida KT2440, the strain was grown in a bioreactor containing AH4 medium as the sole carbon and energy source. Growth was measured turbidimetrically and demonstrated that the optical density increased over the course of 10 days (FIG. 5). To measure changes in substrate concentration, the optimal wavelength for analysis was first identified. Scans of AH4 medium from 190 nm to 750 nm found that the greatest absorbance was 210 nm (FIG. 6). Spectrophotometric analysis at 210 nm indicated a decrease in substrate concentration concomitant with growth. In order to corroborate the absorbance data, for select time points, the medium was analyzed by LPLC-spectrophotometry. The analyses indicated that the concentration of depolymerized nylon in the medium decreased 80±2 percent over an 8-day period or 9-day period (FIG. 7). Viscometry analysis, used to measure polymer concentrations in solution, indicated that the relative viscosity of AH4 medium decreased from $\eta_r$=1.04±0.03 prior to inoculation with P. putida KT2440 to $\eta_r$=0.98±0.01 after the growth of strain KT2440 in flasks for 6 days. Assessment with Student's t test determined that the reduction was significant (p<0.01).

The ability of representative industrial microorganisms to use AH4 as a growth substrate was examined (Table 1). Growth of each microorganism was shown on AH4 medium. For example, experiments with P. putida KT2440 demonstrated that its biomass steadily increased over the course of the experiment. Y. lipolytica, however, grew more robustly in the yeast supplemented (5 mg L$^{-1}$ yeast extract) media.

Figure 8:
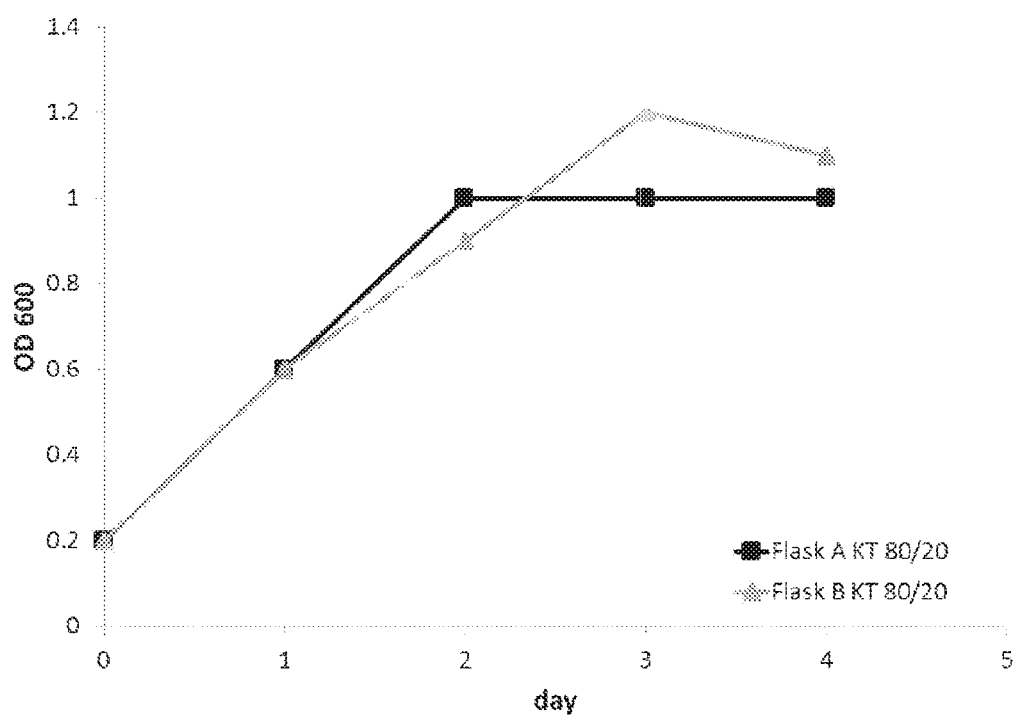
FIG. 8 is a graph showing *P. putida* KT2440 growth in flasks using 80:20 nylon:wool medium. Experiment was carried out in duplicate.
Figure 9:
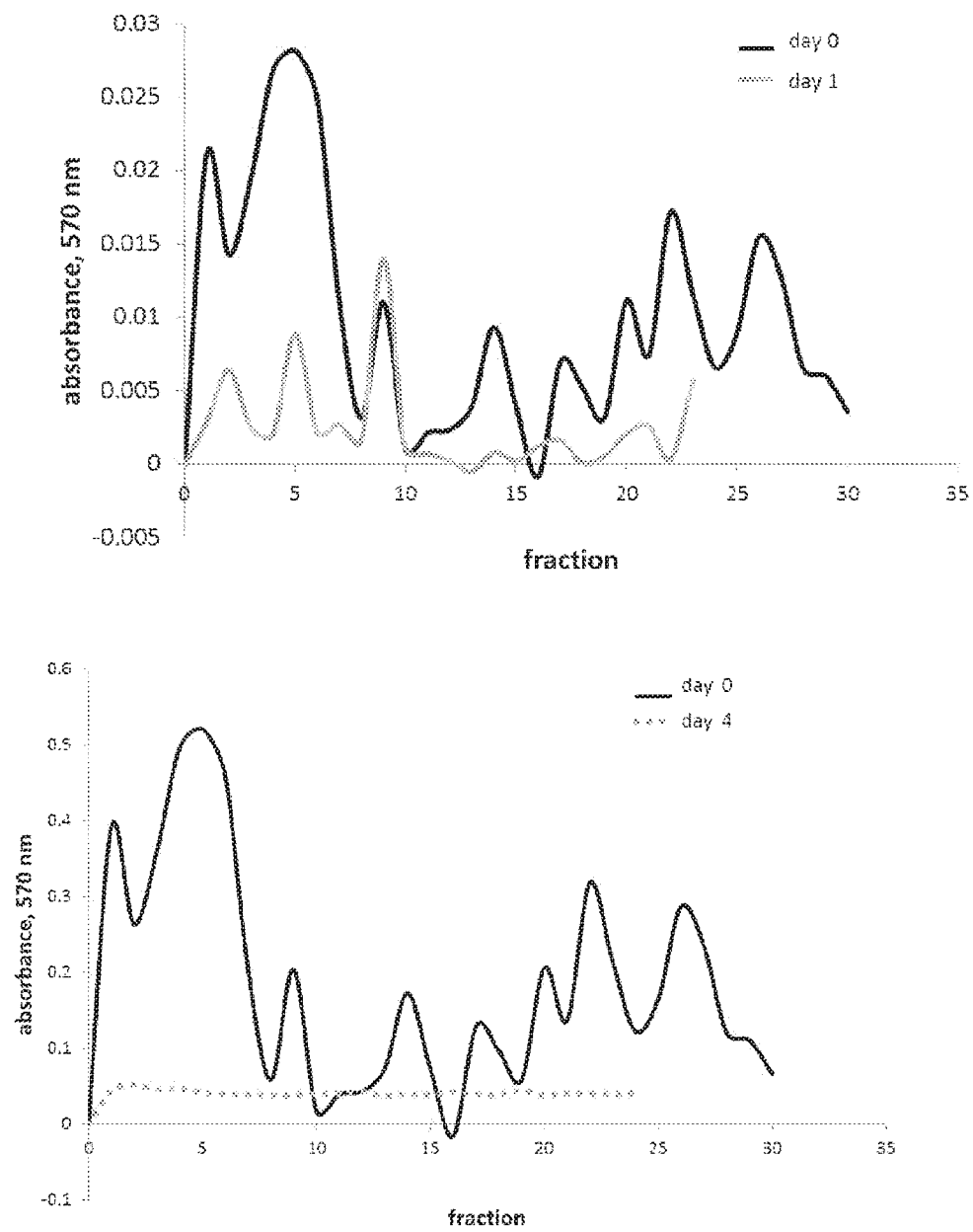
FIG. 9 is a graph showing an LPLC-spectrophotometric analysis of 80:20 nylon:wool medium utilization by *P. putida* KT2440 during bioreactor growth. Upper panel: substantial biodegradation is evident after 4 days. Lower panel: data are plotted on separate axes to highlight similar peak profiles in the chromatograms for day 0 and day 4.

To determine whether a mixed polymer product could be transformed into a growth substrate by acid hydrolysis, fibers from a nylon-wool blended carpet (80% nylon, 20% wool) were collected and treated by acid hydrolysis and mixed with M9 analogously to AH4 medium. The process resulted in a complex mixture of molecules relative to AH4 (FIG. 4C). The resultant medium was used as the sole carbon and energy source to grow P. putida KT2440 in a bioreactor over a 4-day period (FIG. 8). The optical density of the culture reached 1.1±0.1 (600 nm) on day 3 when measured turbidity leveled off. Substrate consumption was measured by LPLC-spectrophotometry and indicated substantial biodegradation of the medium over the 4-day period (FIG. 9).

TABLE 1

Specific growth rates of select microorganisms using AH4 medium as a carbon and energy source

| Strain | Max. specific growth rate, hr$^{-1}$ | biomass at start of experiment[a] | biomass at end of experiment | growth period, days |
|---|---|---|---|---|
| Yarrowia lipolytica (AH4 + YE)[b] | 0.205 | 0.01 | 2.02 | 6 |
| Yarrowia lipolytica (YE only)[c] | 0.090 | 0.01 | 0.07 | 6 |
| Streptomyces sp. str. BAS1 | 0.067 | 50 mg | 220 mg | 13 |
| Bacillus subtilis str. 6051 | 0.062 | 0.05 | 0.29 | 3 |
| Rhodococcus rhodochrous str. DAP 96253 | 0.013 | 0.19 | 0.34 | 2 |
| Penicillium roqueforti | 0.009 | 10 mg | 50 mg | 7 |
| Pseudomonas putida KT2440 | 0.005 | 0.15 | 0.80 | 10 |

[a]The biomass of Streptomyces and Penicillium was measured as mg wet weight. The biomass of all others was measured as OD$_{600}$
[b]Growth medium contained 2 g L$^{-1}$ nylon and 5 mg L$^{-1}$ yeast extract (YE)
[c]Growth medium contained 5 mg L$^{-1}$ YE only Example 2

Preparation of Olive Oil-HDPE Growth Medium (OP1)

Chemicals: Kroger brand of extra virgin olive oil was used in this work (Kroger, USA). Bags synthesized from HDPE were obtained from Kroger, USA. SDS was obtained from Amersham Biosciences AB, Sweden.

Figure 2:
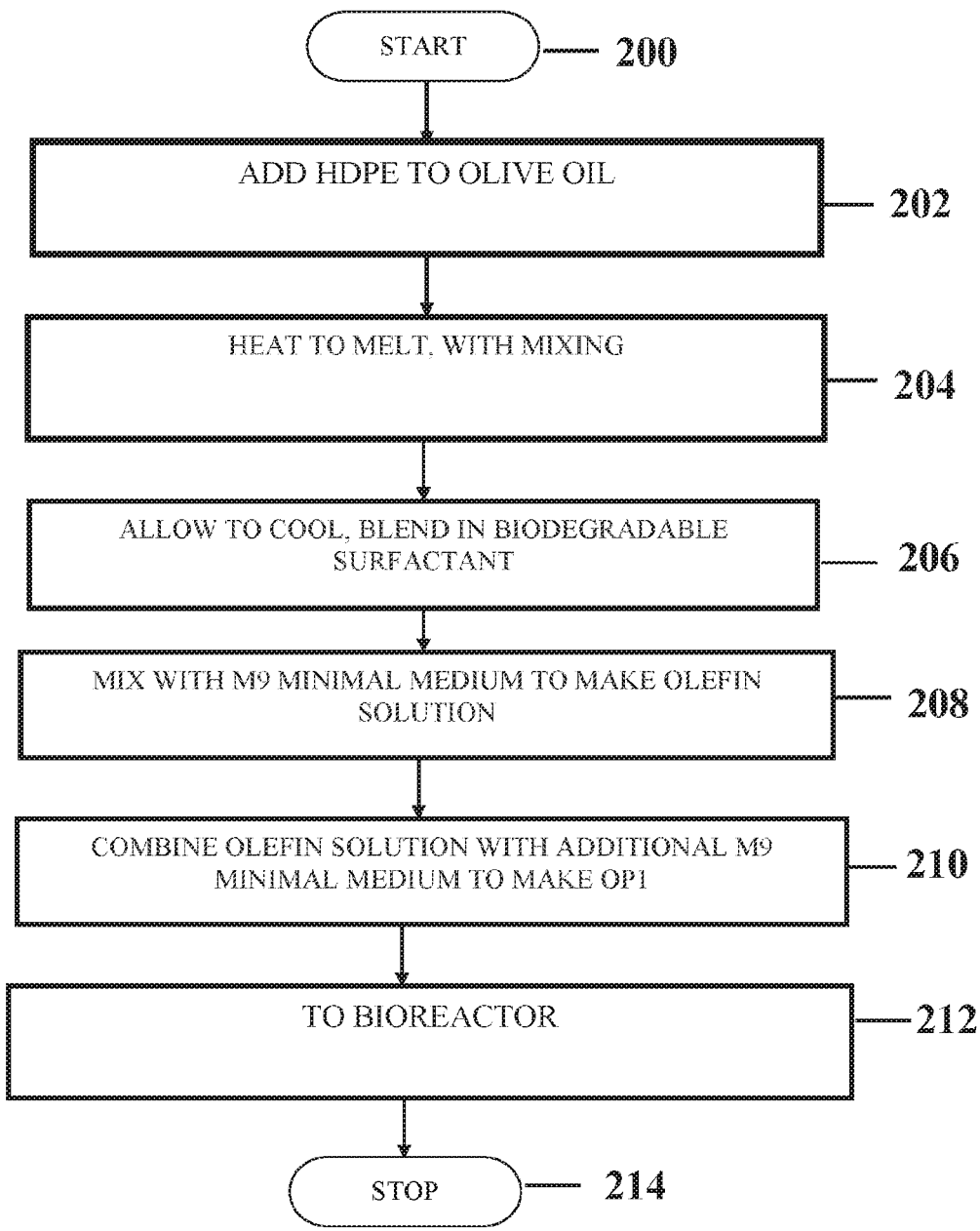
FIG. 2 is a flowchart depicting an exemplary method of preparing HDPE culture medium.

Preparation of OP1 medium: Under a fume hood, on a hotplate, 1 gram of HDPE was heated in a 300 mL Pyrex beaker until the HDPE reached its melting point and formed liquid. Five milliliters of olive oil was then added and mixed until any lumps of plastic present was dispersed in the oil. The temperature of the mixture was maintained at approximately 200° C. An additional 5 mL of olive oil was added and the mixture heated for an additional 10 minutes. The mixture was then removed from the hot plate and allowed to stand for 20 minutes. Seven milliliters of 10% SDS was added to the resulting wax oil/HDPE mixture and the mixture stirred for 20 minutes. To the resulting cottage cheese-like material, 200 mL of M9 salts (no carbon source) were added. The resulting mixture was turbid and had a greenish color. The mixture was autoclaved at 121° C. at 15 psi for 15 min and then added to 800 mL of autoclaved M9. The preparation of the OP1 medium is detailed in FIG. 2.

Bacterial Growth and Substrate Metabolism in OP1 Medium

Inocula preparation: All bacteria were stored at −80° C. Pseudomonas putida KT2440 was cultivated from stock originating in the ATCC culture collection. Inocula were grown overnight from frozen stock in 30-50 mL LB broth in an Erlenmeyer flask at 30° C. The resulting cell suspension was washed once in M9 or 50 mM phosphate buffer prior to use.

Bioreactor operation: A 450 mL bioreactor was used for growth experiments. All components of the bioreactor were autoclaved prior to use. Growth experiments were conducted at 30° C. with a mixing speed of 150 rpm. The pH of the medium was maintained at 7.2-7.5. Filter sterilized sparged air was continuously added to the bioreactor. The average duration of each reaction was 7-11 days. The bioreactor was sampled via a sampling port and data on pH and temperature were continuously collected via a data logging device.

OP1 batch culture experiments: The growth of *P. putida* KT2440 in OP1 medium was investigated using batch culture. Sterile 250 mL Erlenmeyer flasks containing 50 mL of OP1 were inoculated with *P. putida* KT2440 at cell densities ranging from $5.5 \times 10^5$ to $6.6 \times 10^5$ CFU mL$^{-1}$. The inoculated flasks were incubated at 30° C. with 200 rpm shaking. On day 1 and day 4, 1 mL of the culture was collected from each flask and centrifuged at 13,000 rpm for 3 min. The resultant pellet was resuspended in 100㎕ of 50 mM phosphate buffer and was enumerated by serial dilution and plate count.

LPLC-Sudan Black assay: Culture supernatant from the OP1 flask experiments was collected and 1 mL was centrifuged for 5 minutes at 12,000 rpm. The supernatant was taken out and placed in a fresh 1.5 mL tube. A ratio of 100㎕ of prepared Sudan B Black dye was added to 900㎕ of centrifuged supernatant. Samples were vortexed to mix and were fractionated in the same fashion as the ninhydrin assay. Fractionated samples were transferred to microtiter plates and were analyzed at 595 nm on a Victor³ plate reader.

Figure 10:
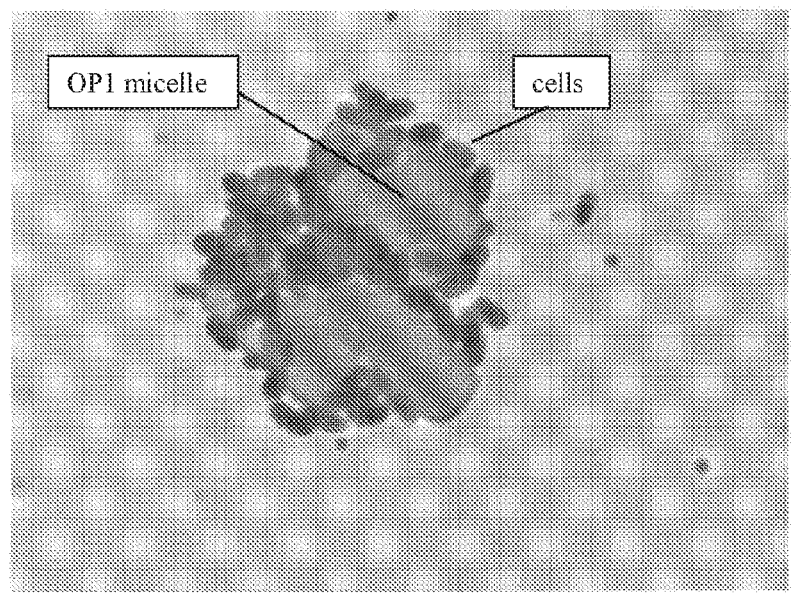
FIG. 10 is an image showing *P. putida* KT2440 growth on OP1 medium. Bright field microscopy; cells stained with crystal violet. Magnification: 400×.
Figure 11:
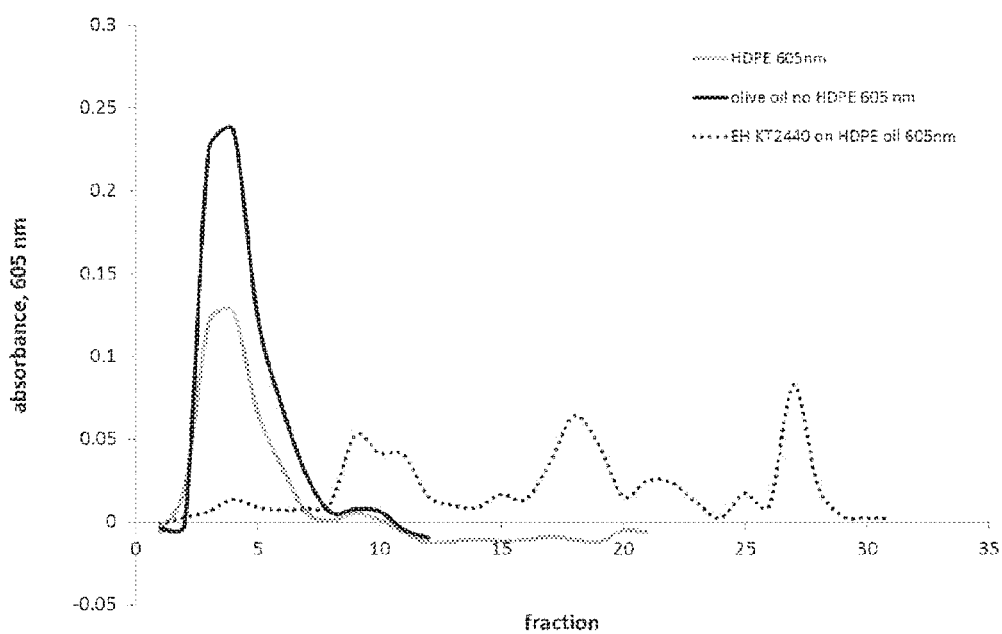
FIG. 11 is a graph showing LPLC spectrophotometric analysis of OP1 substrate utilization by *P. putida* KT2440 grown in batch culture. Black, olive oil only; gray, olive oil +HDPE only; dotted line, olive oil+HDPE+KT2440 cells. Representative data; experiments carried out in duplicate.

Results:

Microbial growth in OP1 medium: Growth of *P. putida* KT2440 in OP1 was examined by microscope and revealed clusters of cells aggregated around colloidal OP1 droplets in the aqueous medium (FIG. 10). Substrate utilization was measured by fractionation of the spent medium using a hydrophobic interaction column, followed by staining of the collected fractions with Sudan Black and measuring absorbance spectrophotometrically. These data revealed extensive reduction of the substrate following 8 days of microbial growth (FIG. 11). Analysis of uninoculated media found that complexation of the Sudan Black with the oil-HDPE mixture resulted in slightly less absorbance than that measured for the oil-alone control. After 8 days of microbial growth, the absorbance of the spent media was at background levels for both the oil-HDPE mixture and the oil-only control, indicating that extensive metabolism had occurred.

Example 3

Development of a Polypropylene-Based Growth Medium

Preparing OP3 Growth Medium from Polypropylene

The following protocol can be used for preparing growth media from polypropylene (PP) and other hydrophobic plastics including polyethylene and potentially PET and PTT, for microorganisms. The source of the polymer can be any source including plastics such as postconsumer waste plastics. In the example below, polypropylene was used from a carpet waste. The polypropylene carpet face fibers are removed from the carpet backing, weighed and then incorporated into production of the growth medium, herein referred to as "OP3". The following protocol is to produce a volume of 500 mL of OP3. It is expected that the protocol can be used to prepare larger volumes. The following protocol involves two glass vessels, vessels A and B. Future versions may potentially be carried out in a single vessel.

Chemicals: polypropylene, dispersant mix (3 mL oleic acid, 0.25 g AH4 resin [derived from nylon 6,6 carpet], 500 mL distilled deionized water), distilled deionized water, yeast extract, sodium dodecyl sulfate (SDS), neat (pure) oleic acid, stir/heat plate, stir bar, screw top bottles.

Preparation of OP3 medium: Polypropylene (PP) obtained from waste carpet was heated in a 500 mL borosilicate glass vessel. The PP was allowed to melt into a clear liquid to which was added 1 mL of the OP3 dispersant mix (as defined above). The mixture was stirred and then removed from the heat source. The PP mixture was stirred until cloudy (for about 10 minutes) and then heated again to about 300° C. The mixture was removed from the heat source after a translucent liquid was observed. An additional 2 mL of OP3 dispersant solution was added to the mixture and allowed to cool at room temperature to form a dispersed PP mixture.

The OP3 medium was prepared by combining 500 mL distilled deionized water, 0.45 g of SDS, and 0.3 g of yeast extract powder in a bottle to form a diluent. The diluent was heated and stirred for about 15 min. The dispersed PP was then added to the diluent and the mixture stirred until cloudy. The volume of the dispersed PP-diluent mixture was made up to 1000 mL by adding distilled deionized water. The resulting mixture was autoclaved at 121° C. and 15 psi for 20 min. Tween 80 was added to the autoclaved mixture while hot to form the OP3 medium. The mixture was cooled for about a hour and a half before storing.

Figure 12:
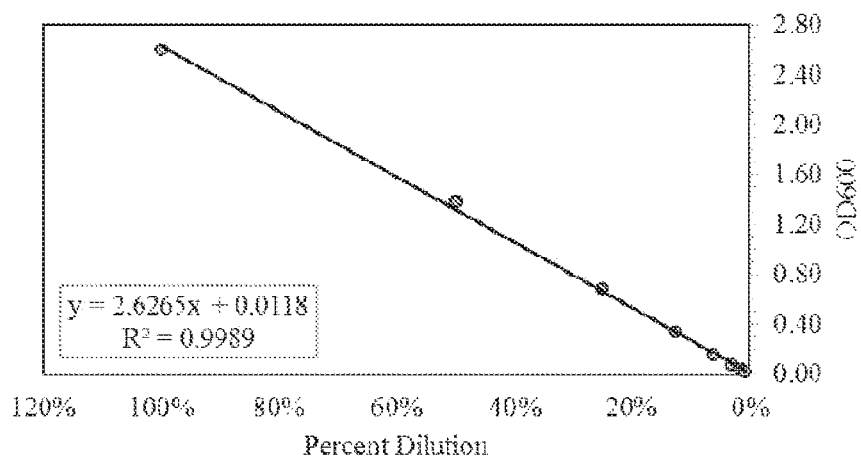
FIG. 12 is a graph showing OP3 absorbance at 600 nm wavelength as a function of its concentration.

Probe for determining the change in OP3 concentration: The change in OP3 concentration was probed by spectrophotometry. A dilution series of OP3 samples was prepared with concentrations of OP3 ranging from 100 percent of the working concentration (1000 mg L$^{-1}$) to 0.8 percent (0.8 mg L$^{-1}$). For each concentration, 100 µL of the OP3 mixture was transferred to a cuvette and diluted with 900 µL of distilled deionized water (DDIH$_2$O). The diluted samples were measured spectrophotometrically at 600 nm. FIG. 12 shows the resulting standard curve. The linear behavior of the curve demonstrated that a decrease in OP3 concentration due to cellular activity can be measured by spectrophotometry.

OP3 uptake by *Yarrowia lipolytica*: A batch culture experiment was carried out to determine whether *Yarrowia lipolytica* could grow in OP3 medium. All materials used in the experiment that came into physical contact with *Y. lipolytica* were autoclaved at 121° C. and 15 psi prior to use, except the UV sterilized plastic cuvettes. First, *Y. lipolytica* frozen stock was thawed at room temperature. A 250 mL Erlenmeyer flask containing 100 mL OP3 medium was inoculated with 20 µL of frozen cell suspension. The inoculated flask was cultured overnight (19-20) hours in an incubator shaker at 150 rpm, 30° C. The culture was then centrifuged at 12,000 rpm for 5 min to form a pellet. The pellet was collected and washed with 50 mM phosphate buffer followed by centrifugation. The resulting pellet was resuspended in 2 mL of 50 mM phosphate buffer. 300 µL aliquots of the cell suspension were added to six 250 mL Erlenmeyer flasks containing 50 mL of OP3 medium—these flasks were the treatments. Three identically prepared flasks with no cells added were prepared—these flasks served as the controls. Both the treated group and the controls were placed in an orbital shaker at 150 rpm and 30° C.

Each flask was sampled over an 8-day period by withdrawing a 1 mL aliquot. Each aliquot was centrifuged in a microfuge at 12,000 rpm for 5 min. The supernatant was removed and the remaining cell pellet resuspended in 1 mL of a 50 mM phosphate buffer. The solution turbidity was measured spectrophotometrically at 600 nm.

Figure 13:
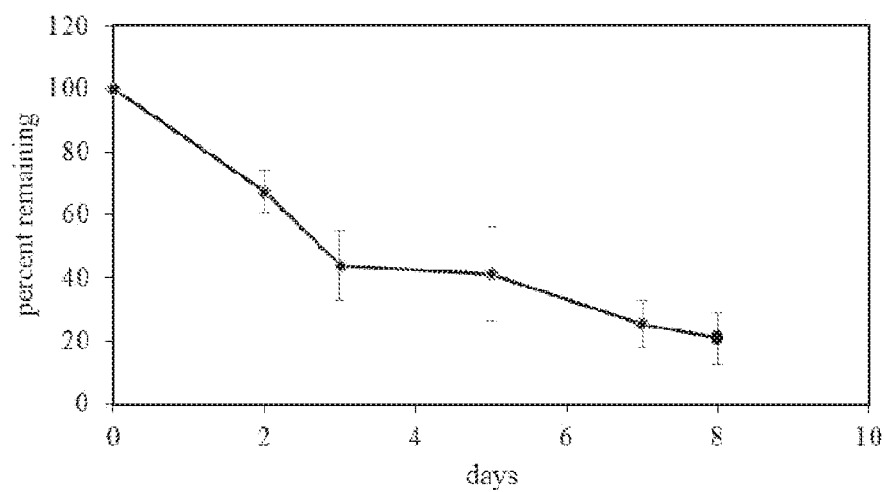
FIG. 13 is a graph showing the change in OP3 concentration over time during *Y. lipolytica* growth. The OP3 concentrations were determined by a spectrophotometer at 600 nm wavelength.

Results:

Cell growth was measured by comparing the initial culture optical density with culture optical density on day 8. The optical density of the initial culture was 0.88±0.15 (SEM). The optical density of the culture at day 8 was 1.44±0.18. The data indicate uptake of OP3 over the course of the experiment. Particularly, the concentration of OP3 on day 8 was only 21±8 percent of the initial OP3 concentration. FIG. 13 shows the change in concentration of OP3 over time. The average percent increase in *Y. lipolytica* culture optical density was 93±41 percent and the corresponding range was 0 to 242 percent, with no change in optical density detected in two flasks and an increase in optical density measured in four flasks.

Figure 14:
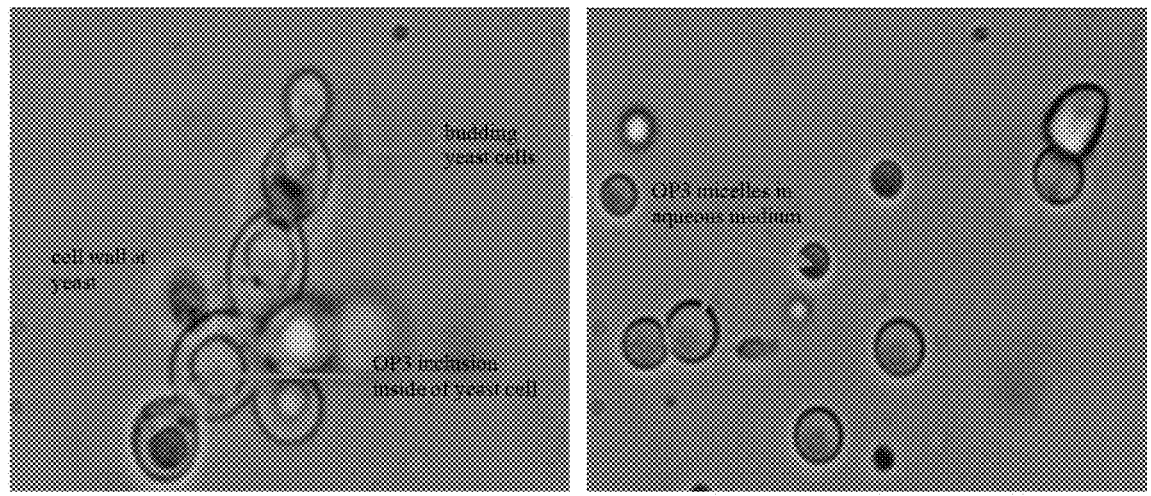
FIG. 14 are bright field microscopic images showing OP3 uptake by *Y.* lipolytica. Magnification: 400×. The image on the left shows uptake of OP3 from the growth medium by *Y. lipolytica* and the image on the right is a control showing OP3 droplets in growth medium with no inoculated cells.

Imaging by bright field microscopy demonstrated OP3 uptake by *Y. lipolytica,* as evidenced by the large droplets contained within the cells (FIG. 14).

Example 4

Microbial Production of Polyhydroxybutyrate During Growth in a Nylon-Derived Growth Medium In this example, a nylon 6,6-derived medium that was less extensively processed and contained a combination of soluble products and colloids (AH2 medium) was investigated for the growth of *Beijerinckia* sp. *Beijerinckia* sp. is a free-living aerobic, chemoheterotrophic microorganism with the ability to synthesize polyhydroxyalkanoates (PHAs; "bioplastics") (Becking 2006) and also measured the corresponding production of Polyhydroxybutyrate (PHB).

Culture isolation and growth: *Beijerinckia* spp was isolated from a compost pile found in Piedmont Park, Atlanta Georgia. The enrichment was carried out using AH2 medium as the sole carbon and energy source. 1 g compost was added to 100 ml AH2 medium and was shaken at 200 rpm and 30° C. for 8 days. Subsequently 1 ml of suspension was transferred to 100 ml AH2 medium and was incubated for 8 days. 10 µl was withdrawn from the suspension and cultured on LB agar plate. Colonies that grew were isolated and were evaluated for the ability to grow in AH2 medium, ultimately yielding a greenish fluorescent mucoid gram negative culture with cells that had dumbbell-shaped morphology and typed to *Beijerinckia* spp using Bergey's Manual, $3r^d$ edition (Kersters and Vancanneyt 2005).

Growth medium: AH2 and AH4 medium were prepared as described herein by depolymerizing N66 carpet face fibers in acid to make their respective concentrates and then mixing the concentrate in M9 salts. AH4 medium is prepared by more extensive acid hydrolysis of AH2 medium and results in a medium free of colloidal material suitable for measurements of growth by optical density. The concentration of AH2 medium was 0.5 g $L^{-1}$ and the concentration of AH4 medium was 1 g $L^{-1}$.

Growth of *Beijerinckia* sp. in AH4 medium: Autoclaved 250 ml Erlenmeyer flasks containing 50 ml of filter sterilized AH4 medium were prepared. The flasks were inoculated with 10 µL of *Beijerinckia* sp. and were grown over a two-day period. After two days, the culture was collected and centrifuged at 20,400×g to remove the culture supernatant and the residues washed with 50 mM phosphate buffer. After inoculation, the flasks were placed in a 30° C. shaker incubator at 150 rpm for 8 days. Changes in substrate concentration were analyzed by UV absorbance spectrophotometry at 210 nm. The experiments were performed in duplicate with each set having one abiotic control (used for the blank in spectrophotometer).

Bioreactor conditions: A 450 ml bioreactor operating in batch mode was used for growth experiments. All components of the bioreactor were autoclaved prior to use. Growth experiments were conducted at 30±1° C. with a mixing speed of 150 rpm. The pH of the medium was maintained at 7.2±0.2. Filter sterilized sparged air was continuously added to the bioreactor. The bioreactor was sampled aseptically via a sampling port and pH and temperature data were continuously collected via a data logging device (Sper Scientific, USA). Samples from the bioreactor were aseptically obtained over 10 days. Growth in the bioreactor was measured spectrophotometrically (600 nm).

Polyhydroxybutyrate (PHB) extraction and analysis: PHBs were extracted from cells grown in the bioreactor at the conclusion of the experiment. The total volume of cell solution in the bioreactor was removed and centrifuged at 20,400×g. The supernatant was removed and a portion of the wet cell mass was collected for PHB extraction. 5.23 grams of wet cell mass was mixed with a 1:1 mixture of 100 percent ethanol and acetone followed by shaking at 100 rpm for 30 min. Afterward, the solvent was removed and the remaining cell mass was mixed with 0.6% sodium hypochlorite at 37° C. for 1 hour with shaking at 100 rpm. The resulting mixture was centrifuged for 10 minutes at 12,000 rpm. The supernatant was collected and the pellet was discarded. The supernatant was then extracted with pure chloroform at a 10:1 ratio (chloroform: supernatant). The chloroform was evaporated at 45° C. using a centrifuge evaporator, leaving a waxy residue at the bottom of the collection tube. (Sayyed, Gangurde et al. 2009) Prior to analysis by gas chromatography, the residue was dissolved in 1.0 ml chloroform. Because any PHB would precipitate during storage, before injection, the mixture was heated in a water bath at 60° C. for up to 20 minutes with vortexing to dissolve.

Gas chromatography: PHB production was measured by flame ionization detection gas chromatography (GC-FID). Analyses were performed with a PerkinElmer Autosystem XL gas chromatograph (PerkinElmer, Wellesley, Mass.), using a Supelco SPB-1 capillary column (length, 60 m, i.d. 0.32 mm; Supelco, Bellefonte, Pa.). The injector temperature was 210° C., and the detector temperature was 220° C. The carrier gas was helium (2.0 ml $min^{-1}$), and detector gases were hydrogen (45 ml $min^{-1}$) and air (450 ml $min^{-1}$). PHB was analyzed with the following temperature program: initial column temperature was 160° C., oven temperature was increased by 8° C. $min^{-1}$ until 200° C.; temperature was held for 10 min. (Braunegg, Sonnleitner et al. 1978).

Microscopy: Growth on nylon colloids was visualized by bright field microscopy and confocal laser scanning microscopy (CLSM). For both types of microscopy, a cover slide chamber was used to obtain a three dimensional image of bacterial growth on the nylon colloid (described below). Bright field microscopy was carried out using an AmScope B120E (AmScope, USA) microscope using a 100x oil immersion objective. Samples for bright field imaging were stained with 0.02% crystal violet. CLSM was conducted with a Zeiss LSM 510 confocal laser scanning microscope (Zeiss, Thornwood, N.Y.) equipped with a Fluor 40× oil immersion lens. For CLSM, samples were stained using 50 uM SYTO 59 nucleic acid stain (Life Technologies, USA). Fluorescence in CLSM images resulted from excitation at 543 nm using the HeNe laser and the 488 nm line of the argon laser. Nylon colloids were imaged using excitation of both lasers at a gain of 64% for the argon laser and 90-100% for the HeNe laser, and appeared blue due to auto fluorescence. *Beijerinckia* sp. cells appeared from the SYTO 59 nucleic acid stain Cover slide chamber: Microorganisms attached to colloidal nylon were imaged by stabilizing colonized colloids using 3 percent agarose in a microscope-slide sized chamber.

The chamber was constructed from two 60×22 mm number 1 coverslips separated by a silicone ring made from 0.89 mm i.d. silicone tubing containing a segment of 22-gauge steel wire. To make the chamber, a 63.5 mm length of tubing was threaded with 76 mm of wire and bent to form a "donut" shape. The ring was placed in the center of the coverslip, attached with a thin coating of Barge toluene-free contact cement (North Brookfield, Mass., USA) and allowed to set overnight.

To image, 10 μl of growth medium containing colonized colloids were placed in a 1.5 ml microfuge tube and stained with 50 μM SYTO 59 for 5 min. After staining, 10 μL of sample was transferred to the chamber using a 1000 μL pipet. 1000 μL of melted 3 percent agarose was quickly placed over the sample and gently tilted to distribute throughout the chamber and to ensure that the sample was in contact with the cover slip. Once the agarose gelled, a thin film of contact cement was place on the silicone ring and a second 60×22 mm cover slip was adhered to it for 20 min, creating a sealed, stained sample that could sit on the stage of the microscope and be manipulated for imaging. (Pittman, Robbins et al. 2010).

Figure 15:
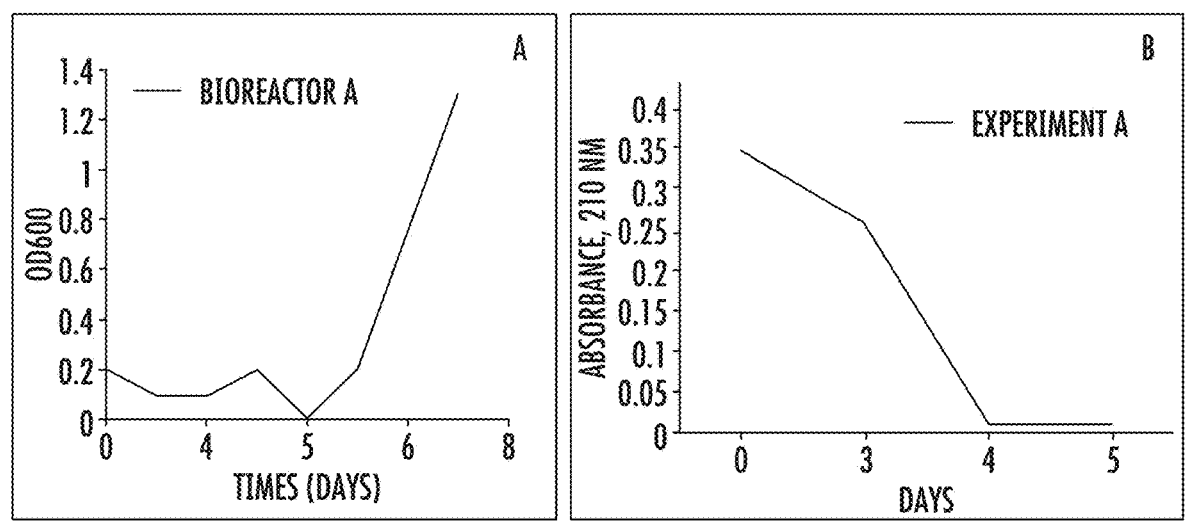
FIG. 15 are graphs showing the substrate utilization during growth of *Beijerinckia* sp. The left graph shows cellular growth in the bioreactor and the right graph shows substrate utilization by of *Beijerinckia* sp. using AH2 medium.
Figure 16:
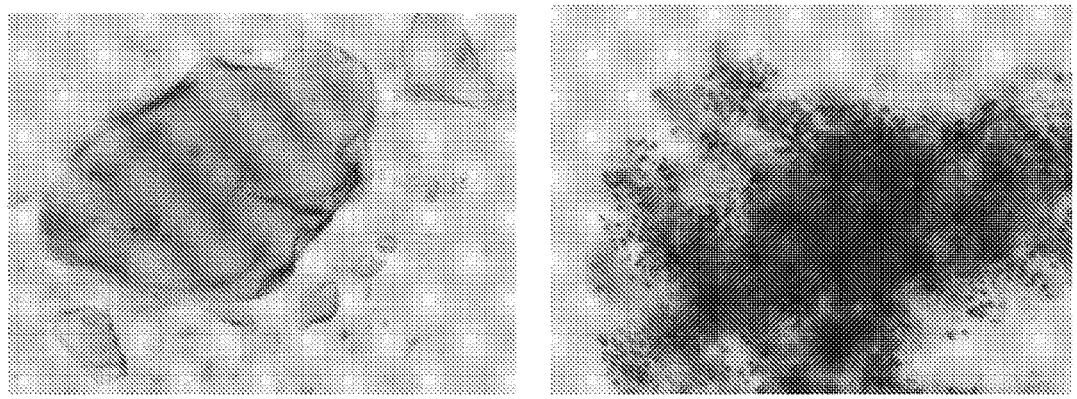
FIG. 16 are images showing growth of *Beijerinckia* sp. on nylon colloids. The image on the left shows uncolonized nylon control and the image on the right shows the colonized sample. All samples were stained with 0.2 percent crystal violet and imaged using bright field microscopy. Magnification: 400×.

Results:

Growth and substrate utilization of nylon-derived media: *Beijerinckia* sp grew on the soluble components of AH2 medium and on suspended nylon colloids present in the medium. To evaluate growth on the soluble components of the medium, *Beijerinckia* sp. was cultivated in a bioreactor over an 8-day period using AH2 medium as the sole carbon and energy source. After an initial decline, the optical density of the medium in the bioreactor increased exponentially after 5 days (FIG. 15). Growth on the colloidal component of AH2 was assessed by bright field microscopy and CLSM. These complementary assays indicated the presence of bacteria growing as biofilms on the surfaces of colloids (see for example FIG. 16). Substrate biodegradation was detected at 210 nm during the growth of Beijerinckia sp. on AH4 medium. The substrate could no longer be detected after 4 days.

Figure 17:
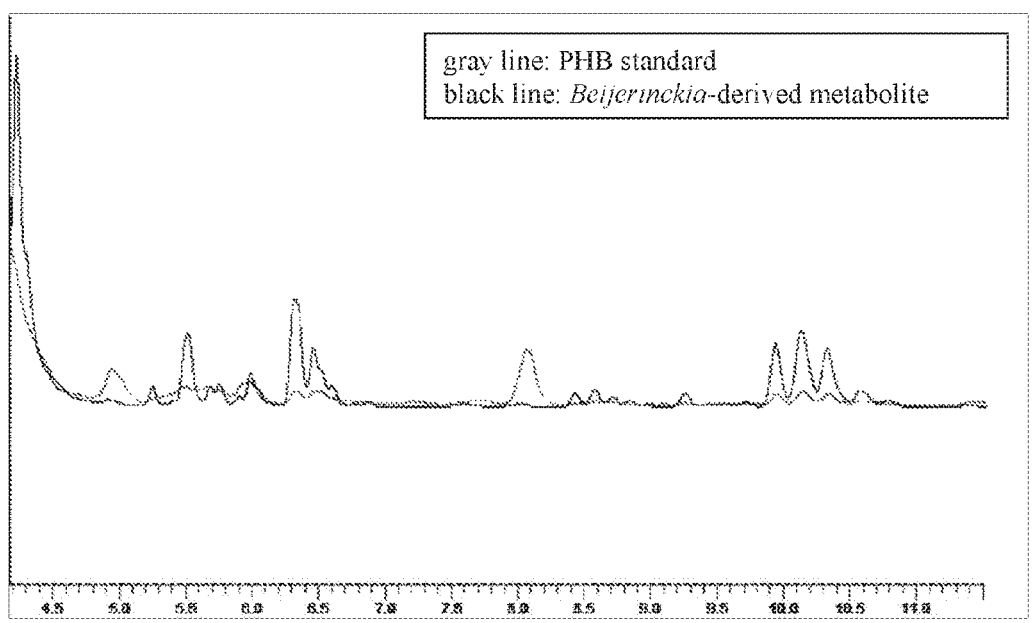
FIG. 17 is a GC-FID spectrum showing PHB production. The black line shows the PHB control (0.15 g mL$^1$) and the gray line shows the PHB extracted from *Beijerinckia* sp. grown in the bioreactor.

PHB production: The presence of PHB was readily detected following Nile blue staining, visible as a bright yellow color in contrast with the red-stained bacteria (data not shown). A comparison of extracted PHB with a 0.150 grams of commercial PHB standard by GC-FID indicated the presence of several recognizable peaks. Two prominent peaks that were not homologous to the PHB standard were also detected (FIG. 17).

The findings indicate that a waste plastic can serve as a growth substrate for a bioconversion process if the plastic is sufficiently depolymerized to increase its bioavailability. Beijerinckia sp. was shown to act as a biocatalyst, converting nylon 6,6 into PHB. In sum, this example shows that acid hydrolysis can be used to improve plastic polymer bioavailability. Previous approaches for bioconversion of plastic waste include pyrolysis (Kenny, Runic et al. 2008), melting, dispersal, and enzymatic treatment (Negoro 2000). In the present example, it was shown that PHB could be produced during the growth of Beijerinckia sp. on AH2 medium. It is anticipate that a diversity of products can be made during growth on the nylon-derived media disclosed herein using both wild-type and engineered strains of microorganisms. It is believed that bioprocesses based on soluble media such as AH4 medium are likely to be easier to optimize due to the thoroughly dissolved carbon source, but that AH2 medium could function in select processes and be advantageous due to the predicted lower production costs.

SUMMARY

The presented data in examples 1 through 4 demonstrate different approaches for bioconversion of polymeric materials derived from, for example plastic waste. The examples show that the polymeric materials can serve as a feedstock for the production of value-added products. As such, many waste plastics can be redirected into productive uses as biological substrates. It has been shown that microorganisms can handle mixed polymer wastes, using a single species of microorganisms in some cases, and in others, employing microbial communities to expand the metabolic potential of the system. The growth media described herein will be suitable for natural microbiota and for synthetic biology applications.

The AH4 medium described herein is suitable for diverse microorganisms and can be used as a general growth medium. The AH4 medium will be amenable for packaging to be use in research laboratories and manufacturing facilities. It was shown that acid hydrolysis can be used for products manufactured from diverse polymers, including wool and potentially cellulose. Two methods for bioconversion of hydrophobic plastics were also shown. The production of a bioproduct during growth of a host cell in media derived from polymeric materials such as plastic is feasible.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative materials and method steps disclosed herein are specifically described, other combinations of the materials and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

What is claimed is:

1. A method for producing a biopolymer, the method comprising
   a) introducing a host cell that expresses the biopolymer's biosynthetic pathway into a microbial culture medium,
   b) accumulating the biopolymer in the host cell by culturing the host cell, and
   c) recovering the biopolymer produced by the host cell, wherein the microbial culture medium is prepared from a non-biodegradable polymeric plastic material by a method comprising:
  i) heating the non-biodegradable polymeric plastic material with a solvent to depolymerize and/or disperse the non-biodegradable polymeric plastic material and form a bioavailable polymeric mixture, wherein the solvent comprises an organic acid, an inorganic acid having a boiling point of 150° C. or less, a base, an oil, a non-polar organic solvent, or a combination thereof,
  ii) processing the mixture comprising filtering, neutralizing, evaporating, distilling, rinsing, or a combination thereof to form a resin, and
  iii) combining the resin with one or more adjuvants to form the microbial culture medium.

2. The method of claim 1, wherein the biopolymer is a polyhydroxyalkanoate or polysaccharide.

3. The method of claim 1, wherein the biopolymer is an enzyme.

4. The method of claim 1, wherein the non-biodegradable polymeric plastic material has an average molecular weight of 10,000 D or greater.

5. The method of claim 1, wherein the non-biodegradable polymeric plastic material is derived from a carpet fiber.

6. The method of claim 1, wherein the non-biodegradable polymeric plastic material comprises nylon.

7. The method of claim 1, wherein in step (i) comprises heating the non-biodegradable polymeric plastic material with a solvent at a temperature from 50° C. to 300° C.

8. The method of claim 1, wherein depolymerizing the non-biodegradable polymeric plastic material is not carried out by enzymatic reaction.

9. A method for producing a biological material from a microbial culture media, the method comprising
  a) introducing a host cell that synthesizes the biological material into the microbial culture medium,
  b) accumulating the biological material in the host cell by culturing the host cell, and
  c) recovering the biological material produced by the host cell,
wherein the microbial culture medium is prepared from a non-biodegradable polymeric plastic material by a method comprising:
  i) heating the non-biodegradable polymeric plastic material with a solvent to depolymerize and/or disperse the non-biodegradable polymeric plastic material and form a bioavailable polymeric mixture, wherein the solvent comprises an organic acid, an inorganic acid having a boiling point of 150° C. or less, a base, an oil, a non-polar organic solvent, or a combination thereof,
  ii) processing the mixture comprising filtering, neutralizing, evaporating, distilling, rinsing, or a combination thereof to form a resin, and
  iii) combining the resin with one or more adjuvants to form the microbial culture medium.

10. The method of claim 9, wherein the biological material is a biopolymer.

11. The method of claim 10, wherein the biopolymer is a polyhydroxyalkanoate or polysaccharide.

12. The method of claim 10, wherein the biopolymer is an enzyme.

13. The method of claim 9, wherein the biological material is a cellular metabolite.

* * * * *